(12) United States Patent
Nakamura et al.

(10) Patent No.: US 11,782,061 B2
(45) Date of Patent: Oct. 10, 2023

(54) ARTERIOSCLEROSIS AND CANCER DETECTION METHOD USING DEOXYHYPUSINE SYNTHASE GENE AS INDICATOR

(71) Applicants: FUJIKURA KASEI CO., LTD., Tokyo (JP); National University Corporation Chiba University, Chiba (JP)

(72) Inventors: Rika Nakamura, Kuki (JP); Hideyuki Kuroda, Kuki (JP); Go Tomiyoshi, Kuki (JP); Takaki Hiwasa, Chiba (JP); Masaki Takiguchi, Chiba (JP); Naokatsu Saeki, Chiba (JP)

(73) Assignees: FUJIKURA KASEI CO., LTD., Tokyo (JP); National University Corporation Chiba University, Chiba (JP)

( * ) Notice: Subject to any disclaimer, the term of this patent is extended or adjusted under 35 U.S.C. 154(b) by 67 days.

(21) Appl. No.: 15/524,899

(22) PCT Filed: Nov. 5, 2015

(86) PCT No.: PCT/JP2015/081207
§ 371 (c)(1),
(2) Date: May 5, 2017

(87) PCT Pub. No.: WO2016/072464
PCT Pub. Date: May 12, 2016

(65) Prior Publication Data
US 2017/0343547 A1 Nov. 30, 2017

(30) Foreign Application Priority Data
Nov. 7, 2014 (JP) ................................ 2014-226847

(51) Int. Cl.
| | | |
|---|---|---|
| *G01N 33/53* | (2006.01) | |
| *G01N 33/573* | (2006.01) | |
| *C12Q 1/25* | (2006.01) | |
| *C12Q 1/68* | (2018.01) | |

(52) U.S. Cl.
CPC ............ *G01N 33/573* (2013.01); *C12Q 1/25* (2013.01); *C12Q 1/68* (2013.01); *G01N 33/53* (2013.01)

(58) Field of Classification Search
CPC ............... G01N 33/573; G01N 33/53; G01N 33/57446; G01N 33/6893; G01N 2333/91165; G01N 2800/323; C12Q 1/25; C12Q 1/68; C12Q 1/6883; C12Q 1/6886; C12Q 2600/158; C12N 9/1085; C12Y 205/01046
See application file for complete search history.

(56) References Cited

U.S. PATENT DOCUMENTS

| | | | |
|---|---|---|---|
| 2003/0154032 A1* | 8/2003 | Pittman | C07K 14/4713 702/20 |
| 2008/0267999 A1* | 10/2008 | Tainsky | G01N 33/68 424/277.1 |
| 2009/0022731 A1* | 1/2009 | von Schack | C12Q 1/6883 424/145.1 |
| 2010/0076062 A1 | 3/2010 | Thompson et al. | |
| 2011/0086349 A1 | 4/2011 | Anjomshoaa et al. | |
| 2011/0177089 A1 | 7/2011 | Seko et al. | |
| 2011/0195848 A1* | 8/2011 | Roopra | C12Q 1/6886 506/7 |
| 2011/0236903 A1* | 9/2011 | McClelland | C12Q 1/6886 435/6.14 |
| 2011/0287955 A1* | 11/2011 | Nakamura | C07K 14/47 506/9 |
| 2014/0363422 A1* | 12/2014 | Hayday | A61P 3/10 424/131.1 |

FOREIGN PATENT DOCUMENTS

| | | |
|---|---|---|
| AU | 2013206284 A1 | 7/2013 |
| EP | 2 319 924 A1 | 5/2011 |
| JP | 2012-501650 A | 1/2012 |
| WO | 2005/003721 A2 | 1/2005 |

(Continued)

OTHER PUBLICATIONS

Proto Array (2006; retrieved from https://www.thermofisher.com/content/dam/LifeTech/migration/en/filelibrary/protein-expression/pdfs.par.16180.file.dat/protoarray%20v5%20irbp-fhr.pdf).*
Protoaraay Protein list (retrieved from https://www.thermofisher.com/order/catalog/product/PAH0525101?SID=srch-srp-PAH0525101 on Jul. 21, 2018).*
Colman et al., Res Immunol. Jan. 1994;145(1):33-6).*
American Physiological Society, J Neurophysiol 92, (2004), p. 669-671.*
Mete Civelek et al., "Chronic Endoplasmic Reticulum Stress Activates Unfolded Protein Response in Arterial Endothelium in Regions of Susceptibility to Atherosclerosis", Circulation Research, vol. 105, No. 5, Aug. 28, 2009, pp. 453-461, XP055451755 (total 26 pages).

(Continued)

*Primary Examiner* — Carmencita M Belei
(74) *Attorney, Agent, or Firm* — Sughrue Mion, PLLC

(57) ABSTRACT

The present inventors have surprisingly found that a deoxyhypusine synthase (DHPS) gene, which was previously reported to correlate with prostate cancer and cervical cancer, is highly responsive to arteriosclerosis or digestive system cancer, whereby the gene can be used as a desired marker for arteriosclerosis or digestive system cancer. The present invention has been accomplished on the basis of this finding. Specifically, the present invention provides a method for determining arteriosclerosis or digestive system cancer, which method includes detecting expression of a deoxyhypusine synthase gene in a test sample (preferably a blood sample), and determining arteriosclerosis or digestive system cancer of a test subject from which the test sample has been obtained, on the basis of an increase in the gene expression as an index.

5 Claims, 6 Drawing Sheets

Specification includes a Sequence Listing.

(56) References Cited

FOREIGN PATENT DOCUMENTS

WO 2009/144933 A1 12/2009

OTHER PUBLICATIONS

Sridhar Ramaswamy et al., "A molecular signature of metastasis in primary solid tumors", Nature Genetics, Nature Publishing Group, vol. 33, No. 1, Jan. 2003, pp. 49-54, XP002301651.

Nikki P. Lee et al., "Prognostic significance and therapeutic potential of eukaryotic translation initiation factor 5A (eIF5A) in hepatocellular carcinoma", International Journal of Cancer, vol. 127, 2010, pp. 968-976, XP055165907.

Felix H. Shek et al., "Implications of the Use of Eukaryotic Translation Initiation Factor 5A (eIF5A) for Prognosis and Treatment of Hepatocellular Carcinoma", International Journal of Hepatology, vol. 2012, 2012, pp. 1-6, XP055451923 (total 7 pages).

Feng-wei Wang et al., "Roles of Eukaryotic Initiation Factor 5A2 in Human Cancer", International Journal of Biological Sciences, vol. 9, No. 10, 2013, pp. 1013-1020, XP055342005.

Rika Nakamura et al., "An Anti-Deoxyhypusine Synthase Antibody as a Marker of Atherosclerosis-Related Cerebral Infarction, Myocardial Infarction, Diabetes Mellitus, and Chronic Kidney Disease", SM Atherosclerosis Journal, vol. 1, No. 1, Mar. 27, 2017, pp. 1-9, XP055451757.

Communication dated Feb. 26, 2018, from European Patent Office in counterpart application No. 15857813.8.

Xie et al., "Overexpression of EIF-5A2 is associated with metastasis of human colorectal carcinoma", Human Pathology, vol. 39, 2008, pp. 80-86, XP022383146 (7 pages total).

He et al., "Recurrent genetic alterations in 26 colorectal carcinomas and 21 adenomas from Chinese patients", Cancer Genetics and Cytogenetics, vol. 144, 2003, pp. 112-118, XP0055451929 (7 pages total).

Taylor et al., "Eukaryotic translation initiation factor 5A induces apoptosis in colon cancer cells and associates with the nucleus in response to tumour necrosis factor a signalling", Experimental Cell Research, vol. 313, 2007, pp. 437-449, XP005866970 (13 pages total).

Takada et al., "Screening of DNA copy-number aberrations in gastric cancer cell lines by array-based comparative genomic hybridization", Cancer Science, Japanese Cancer Association, vol. 96, No. 2, 2005, pp. 100-110, XP002452931 (11 pages total).

Guan et al., "Recurrent chromosome changes in 62 primary gastric carcinomas detected by comparative genomic hybridization", Cancer Genetics and Cytogenetics, vol. 123, 2000, pp. 27-34, XP027290956 (8 pages total).

Pack et al., "Molecular Cytogenetic Fingerprinting of Esophageal Squamous Cell Carcinoma by Comparative Genomic Hybridization Reveals a Consistent Pattern of Chromosomal Alterations", Genes, Chromosomes & Cancer, vol. 25, No. 2, 1999, pp. 160-168, XP055053918 (9 pages total).

Yen et al., "Copy number changes of target genes in chromosome 3q25.3-qter of esophageal squamous cell carcinoma: TP63 is amplified in early carcinogenesis but down-regulated as disease progressed ", World Journal of Gastroenterology, vol. 11, No. 9, 2005, pp. 1267-1272, XP002479438 (6 pages total).

Communication dated May 30, 2018 issued by the European Patent Office in counterpart European application No. 15857813.8.

International Preliminary Report on Patentability dated May 18, 2017 in counterpart international application No. PCT/JP2015/081207.

Clement et al., "Differential Expression of eIF5A-1 and eIF5A-2 in Human Cancer Cells", the FEBS Journal, vol. 273, 2006, pp. 1102-1114. (13 pages total).

International Search Report dated Dec. 28, 2015 in counterpart international application No. PCT/JP2015/081207.

Communication, dated Oct. 12, 2019, issued in Chinese Application No. 201580059912.9.

* cited by examiner

[Fig. 1]
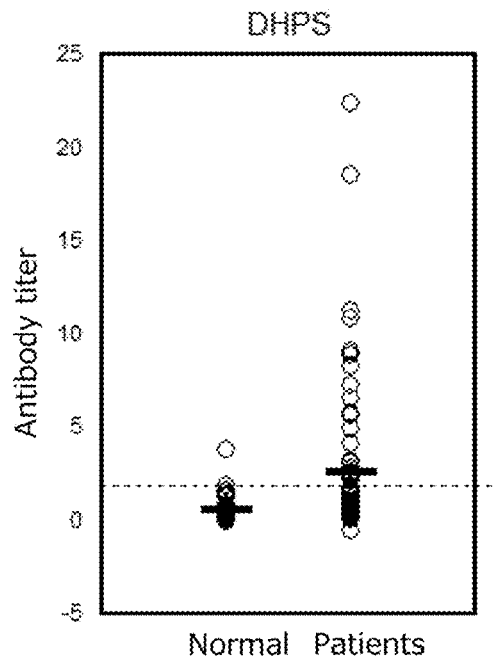
[Fig. 2]
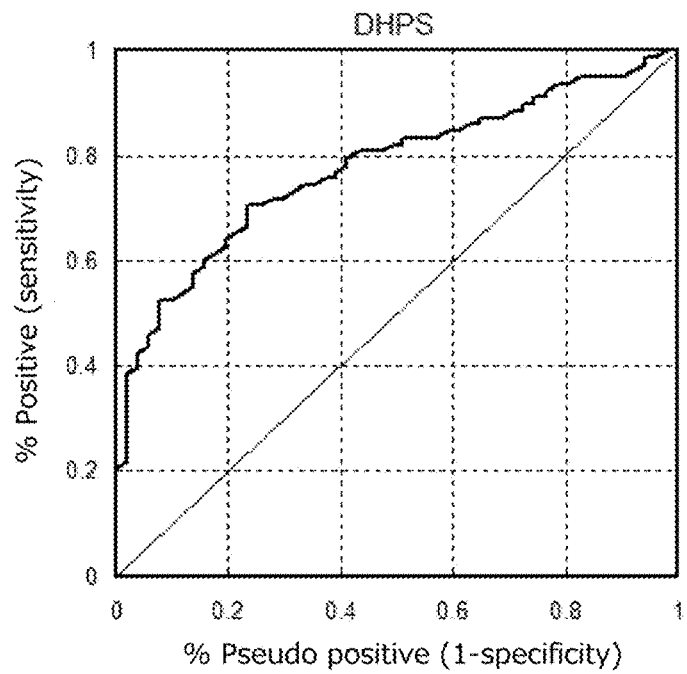

[Fig. 3]
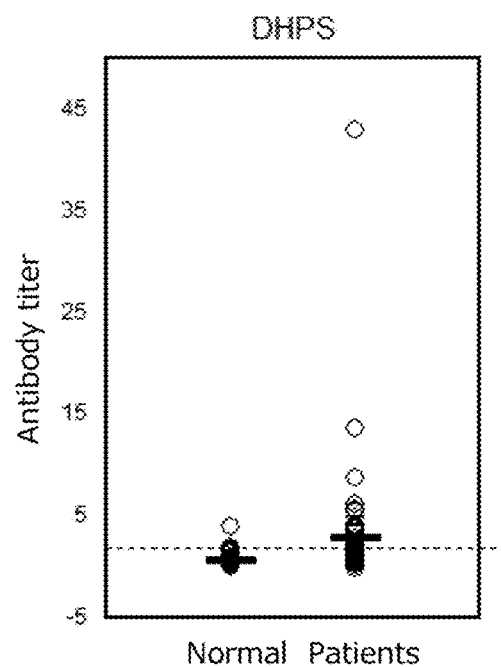
[Fig. 4]
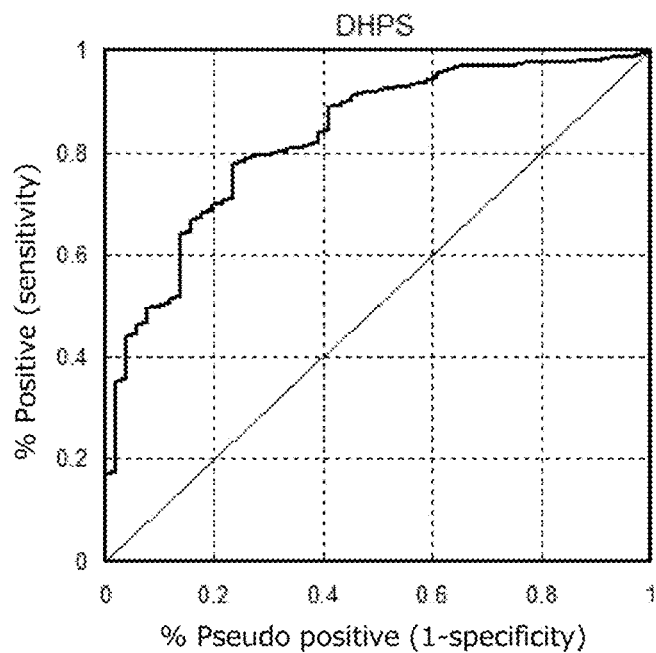

[Fig. 5]
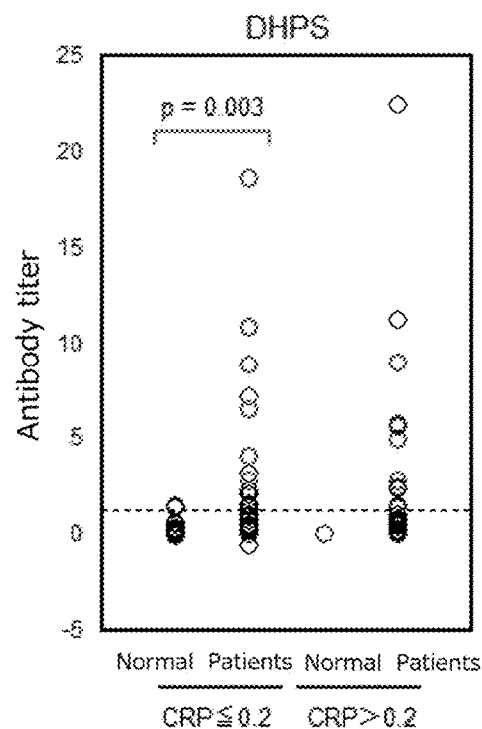
[Fig. 6]
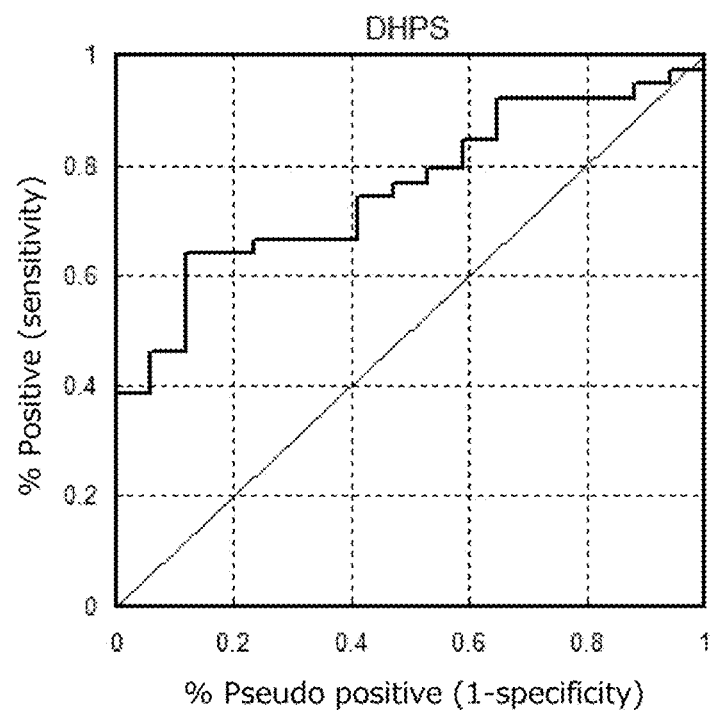

[Fig. 7]
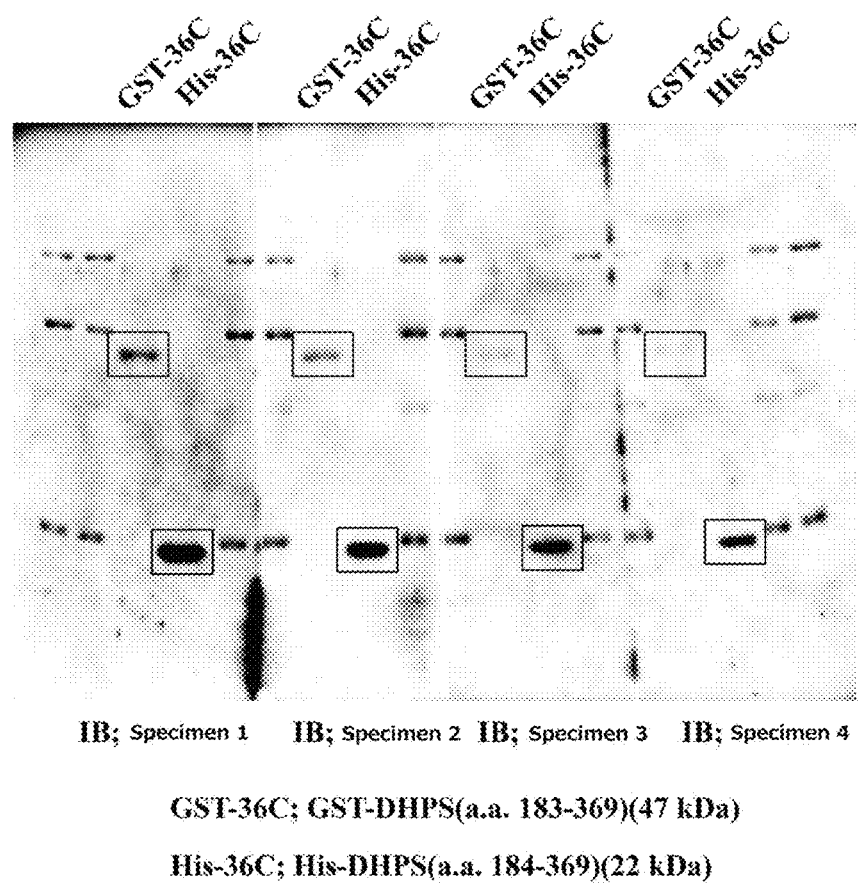
IB; Specimen 1   IB; Specimen 2   IB; Specimen 3   IB; Specimen 4
GST-36C; GST-DHPS(a.a. 183-369)(47 kDa)
His-36C; His-DHPS(a.a. 184-369)(22 kDa)

[Fig. 8]
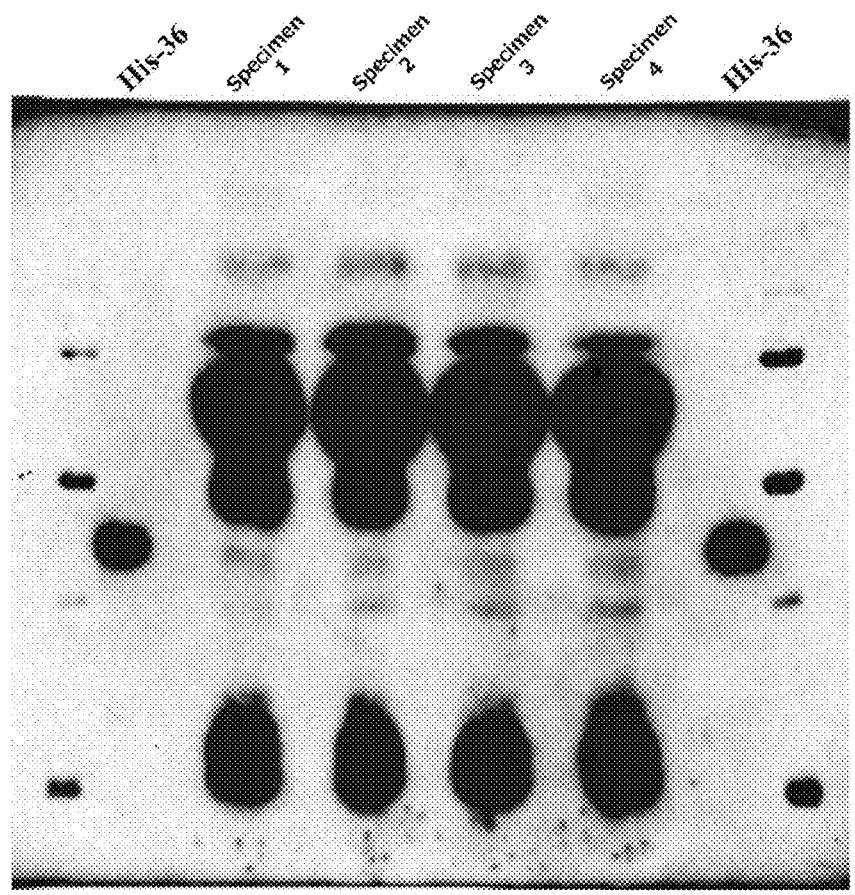
His-36; His-DHPS(a.a. 1-369)(41 kDa)

[Fig. 9]
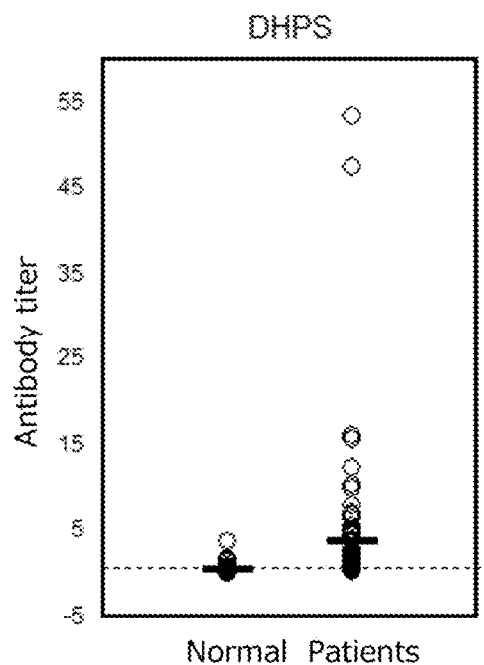
[Fig. 10]
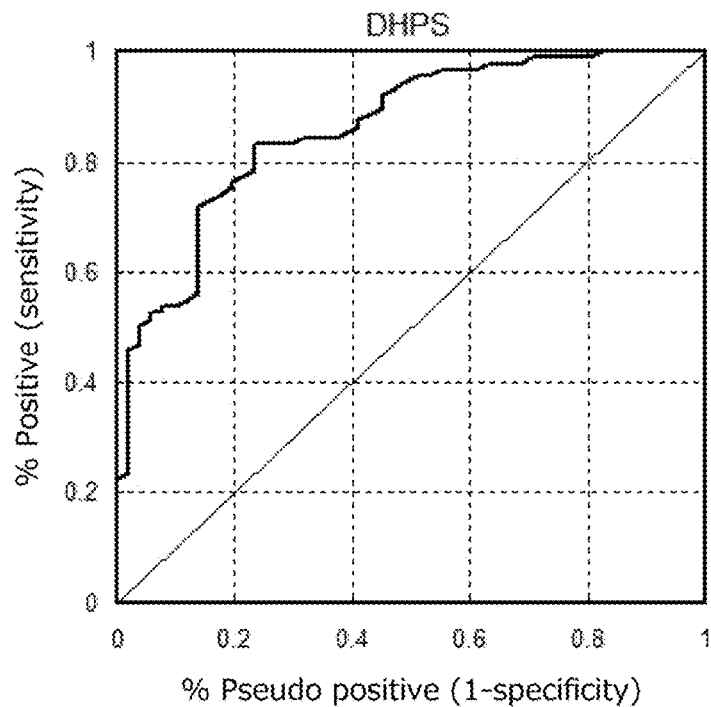

ARTERIOSCLEROSIS AND CANCER DETECTION METHOD USING DEOXYHYPUSINE SYNTHASE GENE AS INDICATOR

CROSS REFERENCE TO RELATED APPLICATIONS

This application is a National Stage of International Application No. PCT/JP2015/081207 filed Nov. 5, 2015 (claiming priority based on Japanese Patent Application No. 2014-226847 filed Nov. 7, 2014), the contents of which are incorporated herein by reference in their entirety.

TECHNICAL FIELD

The present invention relates to a method for detecting a disease or a pathological condition and, more particularly, to a method for detecting arteriosclerosis or a cancer, by use of a deoxyhypusine synthase gene as an index.

BACKGROUND ART

[A] Arteriosclerosis Marker

Nowadays, it is clear that arteriosclerosis is a basal cause for circulatory diseases such as cerebral infarction and myocardial infarction. The risk for such diseases intrinsically increases with aging, and also varies or increases with hereditary factors, unmethodical life style, etc.

Circulatory diseases mainly caused by arteriosclerosis impose burdens on the patient and his or her family. As a result, medical expenses increase from a social aspect. Thus, establishment of means for preventing an onset of circulatory diseases and an appropriate treatment method therefore remain critical issues.

In particular, determination of a hereditary factor therefor enables appropriate provision of preventive treatments including early-stage lifestyle guidance and administration of a prophylactic or treating agent for arteriosclerosis. Therefore, such determination has been more and more important in recent years.

[B] Cancer Marker

The risk for cancers intrinsically increases with aging, and also varies or increases with hereditary factors, unmethodical life style, etc.

An increased number of cancer patients in an aging society causes a serious problem, in that it imposes burdens on the relevant patients and their families. As a result, medical expenses increase from a social aspect. Thus, establishment of means for preventing onset of cancer and an appropriate treatment method therefore remain critical issues.

In particular, determination of a hereditary factor therefor enables appropriate provision of preventive treatments such as early-stage lifestyle guidance. Therefore, such determination has been more and more important in recent years.

PRIOR ART DOCUMENTS

Patent Documents

Patent Document 1: Japanese Patent Application Laid-Open (kokai) No. 2007-14277
Patent Document 2: Japanese PCT Kohyo Patent Publication No. 2006-507816

Non-Patent Documents

Non-Patent Document 1: Cracchiolo B. M., Heller D. S., Clement P. M., Wolff E. C., Park M. H., Hanauske-Abel H. M., "Eukaryotic initiation factor 5A-1 (eIF 5A-1) as a diagnostic marker for aberrant proliferation in intraepithelial neoplasia of the vulva." Gynecol Oncol. 2004 94: 217-22

DISCLOSURE OF THE INVENTION

Problems to be Solved by the Invention

[A] Arteriosclerosis Marker

Arteriosclerosis is caused by various genetic predispositions. Thus, difficulty is encountered in finding a specific gene marker which can reliably and satisfactorily predict arteriosclerosis and which can serve as a so-called "all-purpose marker."

Therefore, there is demand for a gene marker having excellent diagnostic performance in order to thoroughly perform genetic tests for detecting arteriosclerosis.

[B] Cancer Marker

Currently, a part of digestive system cancer such as esophageal cancer and colon cancer exhibit high prevalence, as compared with other cancers. Thus, there is demand for a gene marker having excellent diagnostic performance in order to thoroughly perform genetic tests for detecting digestive system cancer.

Means for Solving the Problems

[A] Arteriosclerosis Marker

Under such circumstances, the present inventors have surprisingly found that a "deoxyhypusine synthase gene," which was previously reported to correlate with prostate cancer and cervical cancer, is highly responsive to arteriosclerosis, whereby the gene can be used as a desired arteriosclerosis marker.

Accordingly, the present invention provides a method for determining arteriosclerosis, which method comprises detecting expression of a deoxyhypusine synthase (hereinafter may be abbreviated as DHPS) gene in a test sample, and determining arteriosclerosis of a test subject from which the test sample has been obtained, on the basis of an increase in the gene expression as an index. Hereinafter, the method may also be referred to as the "arteriosclerosis determination method of the present invention." The test sample employed in the arteriosclerosis determination method of the present invention is preferably a blood specimen. The arteriosclerosis determination method of the present invention may be defined as a data acquisition method which is characterized by comprising acquiring data regarding expression of a DHPS gene in a test sample and, when an increase in the gene expression is observed, using the data as data showing the presence of arteriosclerosis.

The arteriosclerosis determination method of the present invention is generally categorized into the following three modes (i.e., arteriosclerosis determination methods 1 to 3). These methods may be carried out by means of a kit.

(1) Arteriosclerosis Determination Method of the Present Invention 1

In the arteriosclerosis determination method of the present invention, expression of a DHPS gene (i.e., a target gene) may be confirmed by detecting the entirety or a part of a DHPS protein encoded by the gene, as a target polypeptide. Particularly, the entirety or a part of a DHPS protein is preferably detected by use of an antibody which specifically binds to the protein, preferably a monoclonal antibody.

(2) Arteriosclerosis Determination Method of the Present Invention 2

In the arteriosclerosis determination method of the present invention, expression of the DHPS gene (a target gene) may be confirmed by detecting an antibody (an autoantibody) against DHPS present in a test sample (hereinafter, "antibody against DHPS" and "autoantibody against DHPS" may also be referred to as "DHPS antibody" or "anti-DHPS antibody" and "DHPS autoantibody" or "anti-DHPS autoantibody," respectively). The autoantibody may be detected by, for example, bringing the test sample into contact with an immobilized polypeptide including the entirety or a part of DHPS, and detecting, as a signal, a bond between the antibody (autoantibody) against DHPS present in the test sample and the immobilized polypeptide. The number of amino acid units of the polypeptide which is a part of DHPS included in the immobilized polypeptide may be ½ or more the number of amino acid units of the polypeptide which is the entirety of DHPS, specifically, 184 amino acid units or more, and is preferably 186 or more, more preferably 187 or more. On the premise that the antigenicity of the polypeptide is ensured, a polypeptide having a shorter length has a tendency to exhibit high peptide stability, and to lead higher sensitivity since the number of the immobilized polypeptides per a unit amount of a polypeptide-immobilized product may be increased.

(3) Arteriosclerosis Determination Method of the Present Invention 3

In the arteriosclerosis determination method of the present invention, expression of the DHPS gene (a target gene) may be confirmed by detecting, as a target nucleic acid (hereinafter, the expression "nucleic acid" encompasses a fragment thereof), the entirety or a part of the DHPS gene, or a nucleic acid complementary to the entirety or a part of the DHPS gene, present in the test sample. The target nucleic acid may be detected by, for example, hybridizing a nucleic acid probe including a nucleic acid having a sequence complementary to the nucleotide sequence of the target nucleic acid with the immobilized or non-immobilized target nucleic acid, and detecting the signal attributed to the hybridization. In this case, the entirety or a part of the DHPS gene or a nucleic acid complementary to the entirety or a part of the gene may be amplified through a gene amplification method such as PCR, and the gene amplification product may be detected as a target nucleic acid.

(4) Arteriosclerosis Detection Kit

The arteriosclerosis determination method of the present invention may be carried out by means of an arteriosclerosis detection kit having elements which enables the determination.

(5) Polypeptide-Immobilized Plate

The present invention also provides a method for using a polypeptide-immobilized plate, the method comprising the following steps (a) to (d). The polypeptide-immobilized plate is used as "an immobilized polypeptide including the entirety or a part of DHPS" in the above arteriosclerosis determination method 2. The steps are:

(a) a step of bringing a plate on which the entirety or a part of artificially prepared DHPS has been immobilized into contact with a blood specimen, to thereby form an antigen-antibody bound product in which an autoantibody against DHPS present in the blood specimen is bound to the entirety or a part of DHPS on the plate;

(b) a step of binding an antibody-binding and labelled secondary antibody to the autoantibody in the antigen-antibody bound product present on the plate;

(c) a step of developing the label of the secondary antibody bound to the autoantibody on the plate, to thereby detect a developed signal; and (d) a step of counting the developed signal on the plate as a quantification value of the autoantibody against DHPS, and employing the quantification value as an index for arteriosclerosis in the blood specimen when the quantification value is greater than a statistically obtained threshold for arteriosclerosis.

Similar to the case of the above arteriosclerosis determination method 2, the number of amino acid units of the polypeptide which is a part of DHPS immobilized on the plate is preferably ½ or more the number of amino acid units of the polypeptide which is the entirety of DHPS.

Examples of the plate (substrate) onto which the entirety or a part of DHPS is immobilized include a glass slide, a porous gel, and a micro-titer plate. The entirety or a part of DHPS may be immobilized onto the substrate through a known technique. Examples of the technique include antibody-binding techniques such as physical adsorption, covalent binding, ionic binding, and biochemically specific binding. Also, a substrate suited for the immobilization technique to be used may be employed. For example, a substrate having an amino-group-modified surface may be used in order to promote binding of protein on the substrate. In one specific mode, glutaraldehyde is bound to the amino groups on the substrate, and terminal amino groups or the like of the entirety or a part of DHPS is bound to the glutaraldehyde. In another mode, the entirety or a part of DHPS is immobilized onto the amino groups on the substrate through electrostatic interaction. Alternatively, a variety of commercially available substrates suited for immobilizing protein may also be employed.

The "deoxyhypusine synthase (DHPS)," which is a target component of the arteriosclerosis determination method of the present invention, is a known enzyme protein which is known to be related to prostate cancer or cervical cancer (see Patent Document 1 and Non-Patent Document 1) and to apoptosis (see Patent Document 2). The amino acid sequence of a human DHPS is known to be represented by SEQ ID NO: 1 (Patent Document 1), and the nucleotide sequence of the DHPS gene coding therefor is known to be represented by, for example, SEQ ID NO: 2. Furthermore, antibodies (a monoclonal antibody and a polyclonal antibody) against DHPS are also known and may be produced through a conventional method. Commercial products thereof are available. The DHPS (also called DHPS protein) of the present invention is a protein having an amino acid sequence represented by SEQ ID NO: 1, or a protein having an amino acid sequence equivalent to SEQ ID NO: 1, except that one or several amino acids are substituted, deleted, inserted, or added, and having substantially the same biological activity as that of the protein having an amino acid sequence represented by SEQ ID NO: 1. The DHPS gene of the present invention has a nucleotide sequence encoding the above DHPS.

As disclosed in Patent Document 1, DHPS is an enzyme which activates eIF5A (eukaryotic translation Initiation Factor 5A) in the presence of spermidine, to form hypusine. The steric structure of DHPS includes an enzyme active site (i.e., a main structure), a chain structure, and a spherical structure, wherein the enzyme active site and the spherical structure are linked via the chain structure. Through a stearic structure analysis or the like, the enzyme active site and the spherical structure have been found to have a certain interaction, and the spherical structure is presumed to serve as a pseudo-substrate of the enzyme active site. Formation of hypusine is known to be an essential step in cytofunctions, including cell proliferation. In other words, hypusine formation is a post-translation modification step intrinsic to eIF5A; i.e., NAD-dependent transformation of a butylamine moiety of spermidine into a 6-amino group of a specific lysine residue and subsequent hydroxylation. Thus, hypusine formation is essentially observed in the growth of a variety of living things ranging from yeasts to humans.

As described above, possible applications of DHPS particularly as a prostate cancer marker and a cervical cancer marker are known in the art. However, use of DHPS as an arteriosclerosis marker has not been disclosed or suggested.

[B] Cancer Marker

Under such circumstances, the present inventors have surprisingly found that a "deoxyhypusine synthase gene," which was previously reported to correlate with prostate cancer and cervical cancer, is highly responsive to digestive system cancer, whereby the gene can be used as a desired cancer marker.

Accordingly, the present invention provides a method for determining cancer, which method comprises detecting expression of a deoxyhypusine synthase (hereinafter may be abbreviated as DHPS) gene in a test sample, and determining digestive system cancer of a test subject from which the test sample has been obtained, on the basis of an increase in the gene expression as an index. Hereinafter, the method may be referred to also as the "cancer determination method of the present invention." The test sample employed in the cancer determination method of the present invention is preferably a blood specimen. The cancer determination method of the present invention may be defined as a data acquisition method which is characterized by comprising acquiring data regarding expression of a DHPS gene in a test sample and, when an increase in the gene expression is observed, using the data as data showing the presence of digestive system cancer.

The cancer determination method of the present invention is generally categorized into the following three modes (i.e., cancer determination methods 1 to 3). These methods may be carried out by means of a kit.

(1) Cancer Determination Method of the Present Invention 1

In the cancer determination method of the present invention, expression of a DHPS gene (i.e., a target gene) may be confirmed by detecting the entirety or a part of a DHPS protein encoded by the gene, as a target polypeptide. Particularly, the entirety or a part of a DHPS protein is preferably detected by use of an antibody which specifically binds to the protein, preferably a monoclonal antibody.

(2) Cancer Determination Method of the Present Invention 2

In the cancer determination method of the present invention, expression of the DHPS gene (a target gene) may be confirmed by detecting an antibody (an autoantibody) against DHPS present in a test sample (hereinafter, "antibody against DHPS" and "autoantibody against DHPS" may also be referred to as "DHPS antibody" or "anti-DHPS antibody" and "DHPS autoantibody" or "anti-DHPS autoantibody," respectively). The autoantibody may be detected by, for example, bringing the test sample into contact with an immobilized polypeptide including the entirety or a part of DHPS, and detecting, as a signal, a bond between the antibody (autoantibody) against DHPS present in the test sample and the immobilized polypeptide. The number of amino acid units of the polypeptide which is a part of DHPS included in the immobilized polypeptide may be ½ or more the number of amino acid units of the polypeptide which is the entirety of DHPS, specifically, 184 amino acid units or more, and is preferably 186 or more, more preferably 187 or more. On the premise that the antigenicity of the polypeptide is ensured, a polypeptide having a shorter length has a tendency to exhibit high peptide stability, and to lead higher sensitivity since the number of the immobilized polypeptides per a unit amount of a polypeptide-immobilized product may be increased.

(3) Cancer Determination Method of the Present Invention 3

In the cancer determination method of the present invention, expression of the DHPS gene (a target gene) may be confirmed by detecting, as a target nucleic acid (hereinafter, the expression "nucleic acid" encompasses a fragment thereof), the entirety or a part of the DHPS gene, or a nucleic acid complementary to the entirety or a part of the DHPS gene, present in the test sample. The target nucleic acid may be detected by, for example, hybridizing a nucleic acid probe including a nucleic acid having a sequence complementary to the nucleotide sequence of the target nucleic acid with the immobilized or non-immobilized target nucleic acid, and detecting the signal attributed to the hybridization. In this case, the entirety or a part of the DHPS gene or a nucleic acid complementary to the entirety or a part of the gene may be amplified through a gene amplification method such as PCR, and the gene amplification product may be detected as a target nucleic acid.

(4) Cancer Detection Kit

The cancer determination method of the present invention may be carried out by means of a cancer detection kit having elements which enables the determination.

(5) Polypeptide-Immobilized Plate

The present invention also provides a method for using a polypeptide-immobilized plate, the method comprising the following steps (a) to (d). The polypeptide-immobilized plate is used as "an immobilized polypeptide including the entirety or a part of DHPS" in the above cancer determination method 2. The steps are:

(a) a step of bringing a plate on which the entirety or a part of artificially prepared DHPS has been immobilized into contact with a blood specimen, to thereby form an antigen-antibody bound product in which an autoantibody against DHPS present in the blood specimen is bound to the entirety or a part of DHPS on the plate;

(b) a step of binding an antibody-binding and labelled secondary antibody to the autoantibody in the antigen-antibody bound product present on the plate;

(c) a step of developing the label of the secondary antibody bound to the autoantibody on the plate, to thereby detect a developed signal; and (d) a step of counting the developed signal on the plate as a quantification value of the autoantibody against DHPS, and employing the quantification value as an index for digestive system cancer in the blood specimen when the quantification value is greater than a statistically obtained threshold for digestive system cancer.

Similar to the case of the above cancer determination method 2, the number of amino acid units of the polypeptide which is a part of DHPS immobilized on the plate is preferably ½ or more the number of amino acid units of the polypeptide which is the entirety of DHPS.

Examples of the plate (substrate) onto which the entirety or a part of DHPS is immobilized include a glass slide, a porous gel, and a micro-titer plate. The entirety or a part of DHPS may be immobilized onto the substrate through a known technique. Examples of the technique include antibody-binding techniques such as physical adsorption, covalent binding, ionic binding, and biochemically specific binding. Also, a substrate suited for the immobilization technique to be used may be employed. For example, a substrate having an amino-group-modified surface may be used in order to promote binding of protein on the substrate. In one specific mode, glutaraldehyde is bound to the amino groups on the substrate, and terminal amino groups or the like of the entirety or a part of DHPS is bound to the glutaraldehyde. In another mode, the entirety or a part of DHPS is immobilized onto the amino groups on the substrate through electrostatic interaction. Alternatively, a variety of commercially available substrates suited for immobilizing protein may also be employed.

The "deoxyhypusine synthase (DHPS)," which is a target component of the cancer determination method of the present invention, is a known enzyme protein which is known to be related to prostate cancer or cervical cancer (see Patent Document 1 and Non-Patent Document 1) and to apoptosis (see Patent Document 2). The amino acid sequence of a human DHPS is known to be represented by SEQ ID NO: 1 (Patent Document 1), and the nucleotide sequence of the DHPS gene coding therefor is known to be represented by, for example, SEQ ID NO: 2. Furthermore, antibodies (a monoclonal antibody and a polyclonal antibody) against DHPS are also known and may be produced through a conventional method. Commercial products thereof are available. The DHPS (also called DHPS protein) of the present invention is a protein having an amino acid sequence represented by SEQ ID NO: 1, or a protein having an amino acid sequence equivalent to SEQ ID NO: 1, except that one or several amino acids are substituted, deleted, inserted, or added, and having substantially the same biological activity as that of the protein having an amino acid sequence represented by SEQ ID NO: 1. The DHPS gene of the present invention has a nucleotide sequence encoding the above DHPS.

As disclosed in Patent Document 1, DHPS is an enzyme which activates eIF5A (eukaryotic translation Initiation Factor 5A) in the presence of spermidine, to form hypusine. The steric structure of DHPS includes an enzyme active site (i.e., a main structure), a chain structure, and a spherical structure, wherein the enzyme active site and the spherical structure are linked via the chain structure. Through a stearic structure analysis or the like, the enzyme active site and the spherical structure have been found to have a certain interaction, and the spherical structure is presumed to serve as a pseudo-substrate of the enzyme active site. Formation of hypusine is known to be an essential step in cytofunctions including cell proliferation. In other words, hypusine formation is a post-translation modification step intrinsic to eIF5A; i.e., NAD-dependent transformation of a butylamine moiety of spermidine into a ε-amino group of a specific lysine residue and subsequent hydroxylation. Thus, hypusine formation is essentially observed in the growth of a variety of living things ranging from yeasts to humans.

As described above, possible applications of DHPS particularly as a prostate cancer marker and a cervical cancer marker are known in the art. However, use of DHPS as a digestive system cancer marker has not been disclosed or suggested.

Examples of the digestive system cancer include esophageal cancer, stomach cancer, duodenum cancer, colorectal cancers (including rectal cancer and colon cancer), small intestine cancer, gallbladder cancer, pancreatic cancer, and liver cancer. Particularly, DHPS is a useful marker as esophageal cancer or a colorectal cancer.

Effects of the Invention

According to the present invention, there can be provided arteriosclerosis determination means and digestive system cancer determination means, based on the expression of a deoxyhypusine synthase (DHPS) gene in a test sample.

BRIEF DESCRIPTION OF THE DRAWINGS

[FIG. 1]
A graph showing DHPS autoantibody titers (first results) of blood serum samples of acute cerebral infarction patients and healthy subjects, obtained from a medical facility, with distribution profiles thereof obtained through ELISA, along with a cut-off value.

[FIG. 2]
An ROC curve regarding the distribution profiles of the DHPS autoantibody titers shown in FIG. 1.

[FIG. 3]
A graph showing DHPS autoantibody titers (second results) of blood serum samples of acute cerebral infarction patients and healthy subjects, obtained from medical facilities, with distribution profiles thereof obtained through ELISA, along with a cut-off value.

[FIG. 4]
An ROC curve regarding the distribution profiles of the DHPS autoantibody titers shown in FIG. 3.

[FIG. 5]
A graph showing DHPS autoantibody titers (third results) of blood serum samples of acute cerebral infarction patients and healthy subjects, obtained from a medical facility, with distribution profiles thereof obtained through ELISA, wherein each group being divided into a CRP (i.e., a conventional arteriosclerosis marker)-negative group and a CRP-positive group.

[FIG. 6]
An ROC curve regarding the distribution profiles of the DHPS autoantibody titers of the CRP-negative group shown in FIG. 5.

[FIG. 7]
An electrophoretogram obtained through western blotting of DHPS autoantibodies in blood serum samples of acute cerebral infarction patients.

[FIG. 8]
An electrophoretogram obtained through western blotting of endogenous DHPS in blood serum samples of acute cerebral infarction patients.

[FIG. 9]
A graph showing DHPS autoantibody titers of blood serum samples of cancer patients and healthy subjects, obtained from medical facilities, with distribution profiles thereof obtained through ELISA, along with a cut-off value.

[FIG. 10]
An ROC curve regarding the distribution profiles of the DHPS autoantibody titers shown in FIG. 9.

MODES FOR CARRYING OUT THE INVENTION

[A] the Arteriosclerosis Determination Method of the Present Invention
(1) Provision of Materials in Relation to Deoxyhypusine Synthase (DHPS) Gene As described above, the presence of DHPS is known in humans and other animals. The amino acid sequence of DHPS (SEQ ID NO: 1, in the case of human) and the nucleotide sequence (e.g., SEQ ID NO: 2) coding therefor are known.

Thus, a recombinant DHPS can be produced through a known method based on the known sequences. In one specific procedure, a nucleic acid-amplification primer for amplifying a double-strand DNA having the entirety or a part of the above nucleotide sequence is designed, for example, on the basis of the above nucleotide sequence, and a gene amplification product is yielded as the entirety or a part of the DHPS gene through PCR or a similar technique by use of the nucleic acid-amplification primer. The gene amplification product is inserted into an appropriate vector, and the vector is incorporated into an appropriate host. The transformant in which the vector is incorporated is selected, and subjected to cloning. Through expressing the DHPS gene by use of the transformant, the entirety or a part of a recombinant DHPS is yielded. Alternatively, a DHPS gene obtained from the transformant is incorporated into a vector suitable for gene expression, and the resultant vector is incorporated into a host, to thereby produce a transformant. The DHPS gene is expressed in the thus-produced transformant, to thereby yield a recombinant DHPS. DHPS gene cloning may also be carried out via fabrication of a gene library, without employing a gene amplification technique such as PCR as described above. The amino acid sequence of the recombinant DHPS may optionally be changed from the natural type by subjecting the nucleic acid encoding for a target DHPS to a genetic modification technique such as point mutation introduction, random mutation introduction, or stepwise deleted gene production.

The entirety or a part of DHPS may be produced through a known peptide chemical synthesis method. Examples of the peptide synthesis method include liquid phase peptide synthesis and solid phase peptide synthesis, which have been established as common techniques employed in the art. The solid phase peptide synthesis method may include Boc solid phase synthesis and Fmoc solid phase synthesis, which are generally acceptable as preferred chemical synthesis techniques. Particularly in the case of synthesis of a long-chain peptide, ligation may be employed.

The above-produced DHPS gene may also be used in production of an antibody against DHPS through genetic-immunological technique. The DHPS may be used as a nucleic acid probe employed in the arteriosclerosis determination method of the present invention.

Furthermore, the above-produced DHPS gene may also be used as an immunogen in production of an antibody against DHPS; as an autoantibody-bonding field in carrying out the arteriosclerosis determination method of the present invention through detection of an autoantibody; and as a standard substance in the arteriosclerosis determination method of the present invention.

The antibody against DHPS may be produced through a conventional technique. In one specific mode, DHPS or a DHPS gene, serving as an immunogen, is administered to an immunization animal, whereby an antiserum is formed in the immunization animal. The antiserum can be used as a polyclonal antibody. A monoclonal antibody may be produced by collecting B cells from the immunization animal, producing a hybridoma from the B cells, administering the hybridoma to a host animal, and recovering a resultant target monoclonal antibody from the host animal.

If needed, the aforementioned DHPS gene, DHPS, and antibody against DHPS may optionally be subjected to an appropriate modification or treatment. Examples of the modification include addition of a label substance such as a fluorescent material, a dye, an enzyme, and a radioactive substance. Examples of the treatment include fragmentation of the antibody.

The aforementioned materials in relation to DHPS gene may be a commercially-available product, including a ready-made product and an order-made product.

(2) Arteriosclerosis Determination Method 1 of the Present Invention

A characteristic feature of the arteriosclerosis determination method 1 of the present invention resides in that the method comprises detecting expression of a DHPS gene in a test sample, and determining arteriosclerosis of a test subject from which the test sample has been obtained, on the basis of an increase in the gene expression as an index, wherein expression of the DHPS gene (i.e., a target gene) is confirmed by detecting the entirety or a part of DHPS encoded by the gene, as a target polypeptide. Hereinafter, the entirety or a part of DHPS may be collectively referred to as DHPSes in the arteriosclerosis determination method of the present invention.

Firstly, the DHPSes level of a test sample is determined. When the determined DHPSes level is greater than a standard DHPSes level of a subject exhibiting no arteriosclerosis (hereinafter, the subject may be also be referred to as an arteriosclerosis-free subject, in the arteriosclerosis determination method of the present invention), an increase in expression of the DHPS gene of a test subject from which the test sample has been obtained (hereinafter may be referred to as test sample donor) is confirmed. On the basis of the increase as an index, arteriosclerosis of the test sample donor can be determined. Examples of the test sample which may be used in the arteriosclerosis determination method include blood specimens such as a serum specimen, a plasma specimen, and a whole blood specimen, and urine specimens. Of these, blood specimens are preferred. Also, such blood specimens may be subjected in advance to an appropriate treatment such as a treatment with heparin.

The standard DHPSes level of an arteriosclerosis-free subject (including a cut-off value) may be determined by making a sample group of subjects which have not been found to exhibit arteriosclerosis in a general inspection; determining the DHPSes levels of test samples obtained from the sample group; and subjecting the determined DHPSes levels to statistical processing, to thereby obtain the average, standard deviation, etc. thereof.

No particular limitation is imposed on the method of determining the DHPSes level of a test sample. Examples of the determination method include a quantification method employing an antibody (preferably a monoclonal antibody) which specifically binds to DHPSes. Specific examples include immunoprecipitation, western blotting, immunostaining, EIA, RIA, turbidimetry, nephelometry, latex agglutination turbidimetry, and CLEIA. Alternatively, the DHPSes level may be directly determined through TOF-MASS. Among EIA techniques, ELISA employing an immobilized antibody is particularly preferred. Any of these quantification methods may be carried out through a technique which is established for quantifying DHPSes in a test sample as a quantification target substance. Some of these quantification methods will next be described briefly.

In one mode of the quantification means based on ELISA, a test sample is brought into contact with a DHPS antibody immobilized on a microplate, to thereby bind DHPSes present in the test sample to the immobilized antibody. The DHPSes bound to the immobilized antibody is detected with another DHPS antibody labelled with an enzyme or the like, whereby the quantification can be performed. Alternatively, the DHPSes level of the test sample may be determined through simultaneous reaction of the immobilized antibody, the test sample, and the enzyme-labelled antibody.

In one mode of the quantification means based on immunoprecipitation, a test sample is brought into contact with a DHPS antibody immobilized on beads, to thereby bind DHPSes in the test sample to the immobilized antibody, and the DHPSes bound to the immobilized antibody is separated. The DHPSes in the separated product is detected, whereby the quantification can be performed. The DHPSes quantification method based on immunoprecipitation may be carried out by subjecting the aforementioned separated product to electrophoresis, and causing a labelled DHPS antibody to react with a transferred electrophoresis pattern, to thereby detect bands attributed to DHPSes (i.e., western blotting).

The quantification may also be carried out through a method based on western blotting. In one specific mode, cells are removed from a test sample, and the cell-removed test sample is directly separated through electrophoresis. A labelled DHPS antibody is caused to act on the transferred product thereof, and bands attributed to DHPSes are detected, to thereby quantitate DHPSes in the test sample.

In one mode of the quantification means based on latex agglutination turbidimetry, a test sample is brought into contact with the DHPS antibody bound to latex particles, to thereby form an aggregate of an immune complex through antigen-antibody reaction in the liquid phase, and the turbidity change is measured, whereby the quantification can be performed.

(3) Arteriosclerosis Determination Method 2 of the Present Invention

The arteriosclerosis determination method 2 of the present invention is a method, characterized in that expression of the DHPS gene is confirmed in a test sample, and arteriosclerosis of a test subject from which the test sample has been obtained is determined on the basis of an increase in the gene expression as an index, wherein expression of the DHPS gene (a target gene) is confirmed by detecting a DHPS antibody (a DHPS autoantibody) present in the test sample.

That is, the DHPS autoantibody level of a test sample is determined. When the determined DHPS autoantibody level is greater than a standard DHPS autoantibody level of an arteriosclerosis-free subject, an increase in expression of the DHPS gene of a test subject from which the test sample has been obtained is confirmed. On the basis of the increase as an index, arteriosclerosis of the test sample donor can be determined. Examples of the test sample which may be used in the arteriosclerosis determination method include blood specimens such as a serum specimen, a plasma specimen, and a whole blood specimen, and urine specimens. Of these, blood specimens are preferred. Also, such blood specimens may be subjected in advance to an appropriate treatment such as a treatment with heparin.

The standard DHPS autoantibody level of an arteriosclerosis-free subject (including a cut-off value) may be determined by making a sample group of subjects which have not been found to exhibit arteriosclerosis in a general inspection; determining the DHPS autoantibody levels of test samples obtained from the sample group; subjecting the determined DHPS antibody levels to statistical processing, to thereby obtained the average, standard deviation, etc. thereof.

The DHPS autoantibody level may be determined by, for example, bringing the test sample into contact with an immobilized polypeptide including DHPSes, and detecting, as a signal, a bond between the antibody (autoantibody) against DHPS present in the test sample and the immobilized polypeptide. Specific examples of the quantification method which may be employed in the invention include indirect immunofluorescence, ELISA, western blotting (immunoblotting), turbidimetry, nephelometry, latex agglutination turbidimetry, and CLEIA. Any of these quantification methods may be carried out through a technique which is established for quantifying DHPS autoantibody in a test sample as a quantification target substance. One mode of indirect immunofluorescence (FANA) includes bringing a test sample into contact with a DHPSes-immobilized protein array; binding the immobilized DHPSes to a DHPS antibody in the test sample, to thereby form an immobilized DHPSes-anti-DHPS antibody complex; and bringing the complex into contact with a fluorescent-labelled secondary antibody, to thereby quantify the DHPS autoantibody. In ELISA, quantification is carried out by using an enzyme label instead of the label of the secondary antibody employed in indirect immunofluorescence. A variety of labels may be chosen for the secondary antibody. One mode of western blotting include subjecting DHPSes to electrophoresis on SDS-polyacrylamide gel; transferring the electrophoresis results from the gel to a substrate (e.g., a nitrocellulose membrane); bringing a test sample into contact with the transfer substrate, to thereby form a complex between DHPSes on the transfer substrate and the DHPS antibody present in the test sample; and detecting the complex, whereby the quantification can be performed. In one mode of turbidimetry or nephelometry, a DHPSes-anti-DHPS antibody complex, formed via contact of a test sample with DHPSes, is detected by turbidity (turbidimetry) or a change in scattered light intensity (nephelometry), whereby the quantification can be performed. In one mode of latex agglutination turbidimetry, a test sample is brought into contact with DHPSes-bound latex particles, to thereby form an aggregate of latex particles via interaction between autoantibodies bound to latex particles, and the aggregate is detected, whereby the quantification can be performed. In one mode of CLEIA, a test sample is brought into contact with DHPSes-bound magnetic particles, to thereby form a DHPSes-anti-DHPS antibody complex on the magnetic particles, these particles are magnetically collected, unreacted matter is removed, and an appropriate fluorescent treatment or the like is carried out to detect the complex, whereby the quantification can be performed.

(4) Arteriosclerosis Determination Method 3 of the Present Invention

A characteristic feature of the arteriosclerosis determination method 3 of the present invention resides in that the method comprises detecting expression of a DHPS gene in a test sample, and determining arteriosclerosis of a test subject from which the test sample has been obtained, on the basis of an increase in the gene expression as an index, wherein expression of the DHPS gene (i.e., a target gene) is confirmed by detecting, as a target nucleic acid, the entirety or a part of the DHPS gene, or a nucleic acid complementary to the entirety or a part of the DHPS gene, present in the test sample.

In one specific procedure, the level of mRNA encoding DHPSes in the test sample is determined. When the determined mRNA level is greater than a standard mRNA level of an arteriosclerosis-free subject, an increase in expression of the DHPSes gene of a test subject from which the test sample has been obtained is confirmed. On the basis of the increase as an index, arteriosclerosis of the test sample donor can be determined. Examples of the test sample which may be used in the arteriosclerosis determination method include blood specimens such as a serum specimen, a plasma specimen, and a whole blood specimen, and urine specimens. Of these, blood specimens are preferred. Also, such blood specimens may be subjected in advance to an appropriate treatment such as a treatment with heparin.

The nucleic acid, serving as a basic material in the determination of the level of mRNA encoding DHPSes in the test sample, may be produced by extracting RNA from the test sample through a known technique and reversely transcribing the RNA to the corresponding DNA, to thereby yield a cDNA. The cDNA is subjected to gene amplification such as PCR employing a gene amplification primer for amplifying the DHPSes gene (RT-PCR). Through measuring the mRNA level equivalent (e.g., the copy number of the DHPSes gene in gene amplification at specific cycles, or an increasing rate of the DHPSes gene copy number) as a basic index, the expression level of the DHPSes gene in the test sample can be determined.

The target nucleic acid may be detected by hybridizing a nucleic acid probe including a nucleic acid fragment having a nucleotide sequence complementary to the nucleotide sequence of the target nucleic acid, with the target nucleic acid obtained as an immobilized or non-immobilized gene amplification product, and detecting a signal attributed to hybridization.

The signal may be detected through, for example, southern blotting. Alternatively, a series of steps of the arteriosclerosis determination method 3 of the present invention may be carried out through, for example, a real-time analysis employing RT-PCR.

(5) Arteriosclerosis Detection Kit of the Present Invention

As described above, the arteriosclerosis detection kit of the present invention is a kit having elements for carrying out the arteriosclerosis determination method of the present invention. The elements of the arteriosclerosis detection kit vary in accordance with the mode and purpose of use of the arteriosclerosis determination method of the present invention, the degree of kit design, and other factors.

In one mode of the arteriosclerosis detection kit for carrying out the arteriosclerosis determination method 1 of the present invention, the kit is employed for ELISA, which kit includes a plate on which a DHPS antibody is immobilized as a primary antibody, a labelled secondary antibody, and an agent for developing the label of the secondary antibody. Alternatively, the kit is employed for latex agglutination turbidimetry, which kit contains latex particles onto which a DHPS-antibody is bound. Yet alternatively, the kit is employed for CLEIA, which kit includes magnetic particles onto which a DHPS-antibody is bound, a labelled secondary antibody, and an agent for developing the label of the secondary antibody. The above-mentioned elements of the kits are merely examples, and the present invention also encompasses kits for carrying out other embodiments of the arteriosclerosis determination method 1 of the present invention. Furthermore, it is possible for a similar kit having fewer elements so as to shear with an outsourcing inspection and to self-procurement. Also, another possible embodiment of the kit of the invention is an arteriosclerosis detection kit which has further elements such as a diluent and a tube for an agent, so as to be immediately used. Needless to say, the kit may further include an additional element suited for a specific inspection procedure.

In one mode of the arteriosclerosis detection kit for carrying out the arteriosclerosis determination method 2 of the present invention, the kit is employed for FANA or ELISA, which kit includes a plate on which a DHPSes is immobilized, a labelled secondary antibody against the autoantibody, and an agent for developing the label of the secondary antibody. Alternatively, the kit is employed for latex agglutination turbidimetry, which kit contains latex particles onto which a DHPSes is bound. Yet alternatively, the kit is employed for CLEIA, which kit includes magnetic particles onto which a DHPSes is bound, a labelled secondary antibody against the autoantibody, and an agent for developing the label of the secondary antibody. The above-mentioned elements of the kits are merely examples, and the present invention also encompasses kits for carrying out other embodiments of the arteriosclerosis determination method 2 of the present invention. Furthermore, it is possible for a similar kit having fewer elements so as to shear with an outsourcing inspection and to self-procurement. Also, another possible embodiment of the kit of the invention is an arteriosclerosis detection kit which has further elements such as a diluent and a tube for an agent, so as to be immediately used. Needless to say, the kit may further include an additional element suited for a specific inspection procedure.

In one mode of the arteriosclerosis detection kit for carrying out the arteriosclerosis determination method 3 of the present invention, the kit may include a reverse transcriptase and a reverse transcription primer for reverse transcription of mRNA, a gene amplification primer for amplifying a cDNA encoding DHPSes, a nucleic acid probe for detecting the gene amplification product, and an agent for developing the signal of the nucleic acid probe. The above-mentioned elements of the kits are merely examples, and the present invention also encompasses kits for carrying out other embodiments of the arteriosclerosis determination method 3 of the present invention. Furthermore, it is possible for a similar kit having fewer elements so as to shear with an outsourcing inspection and to self-procurement. Also, another possible embodiment of the kit of the invention is an arteriosclerosis detection kit which has further elements such as a diluent and a tube for an agent, so as to be immediately used. Needless to say, the kit may further include an additional element suited for a specific inspection procedure.

[B] Cancer Determination Method of the Present Invention
(1) Provision of Materials in Relation to Deoxyhypusine Synthase (DHPS) Gene As described above, the presence of DHPS is known in humans and other animals. The amino acid sequence of DPHS (SEQ ID NO: 1, in the case of human) and the nucleotide sequence (e.g., SEQ ID NO: 2) coding therefor are known.

Thus, a recombinant DHPS can be produced through a known method based on the known sequences. In one specific procedure, a nucleic acid-amplification primer for amplifying a double-strand DNA having the entirety or a part of the above nucleotide sequence is designed, for example, on the basis of the above nucleotide sequence, and a gene amplification product is yielded as the entirety or a part of the DHPS gene through PCR or a similar technique by use of the nucleic acid-amplification primer. The gene amplification product is inserted into an appropriate vector, and the vector is incorporated into an appropriate host. The transformant in which the vector is incorporated is selected and subjected to cloning. Through expressing the DHPS gene by use of the transformant, the entirety or a part of a recombinant DHPS is yielded. Alternatively, a DHPS gene obtained from the transformant is incorporated into a vector suitable for gene expression, and the resultant vector is incorporated into a host, to thereby produce a transformant. The DHPS gene is expressed in the thus-produced transformant, to thereby yield a recombinant DHPS. DHPS gene cloning may also be carried out via fabrication of a gene library, without employing a gene amplification technique such as PCR as described above. The amino acid sequence of the recombinant DHPS may optionally be changed from the natural type by subjecting the nucleic acid encoding for a target DHPS to a genetic modification technique such as point mutation introduction, random mutation introduction, or stepwise deleted gene production.

The entirety or a part of DHPS may be produced through a known peptide chemical synthesis method. Examples of the peptide synthesis method include liquid phase peptide synthesis and solid phase peptide synthesis, which have been established as common techniques employed in the art. The solid phase peptide synthesis method may include Boc solid phase synthesis and Fmoc solid phase synthesis, which are generally acceptable as preferred chemical synthesis techniques. Particularly in the case of synthesis of a long-chain peptide, ligation may be employed.

The above-produced DHPS gene may also be used in production of an antibody against DHPS through genetic-immunological technique. DHPS may be used as a nucleic acid probe employed in the cancer determination method of the present invention.

Furthermore, the above-produced DHPS gene may also be used as an immunogen in production of an antibody against DHPS; as an autoantibody-bonding field in carrying out the cancer determination method of the present invention through detection of an autoantibody; and as a standard substance in the cancer determination method of the present invention.

The antibody against DHPS may be produced through a conventional technique. In one specific mode, DHPS or a DHPS gene, serving as an immunogen, is administered to an immunization animal, whereby an antiserum is formed in the immunization animal. The antiserum can be used as a polyclonal antibody. A monoclonal antibody may be produced by collecting B cells from the immunization animal, producing a hybridoma from the B cells, administering the hybridoma to a host animal, and recovering a resultant target monoclonal antibody from the host animal.

If needed, the aforementioned DHPS gene, DHPS, and antibody against DHPS may optionally be subjected to an appropriate modification or treatment. Examples of the modification include addition of a label substance such as a fluorescent material, a dye, an enzyme, and a radioactive substance. Examples of the treatment include fragmentation of the antibody.

The aforementioned materials in relation to DHPS gene may be a commercially available product, including a ready-made product and an order-made product.

(2) Cancer Determination Method 1 of the Present Invention

A characteristic feature of the cancer detection method 1 of the present invention resides in that the method comprises detecting expression of a DHPS gene in a test sample, and determining digestive system cancer of a test subject from which the test sample has been obtained, on the basis of an increase in the gene expression as an index, wherein expression of the DHPS gene (i.e., a target gene) is confirmed by detecting the entirety or a part of DHPS encoded by the gene, as a target polypeptide. Hereinafter, the entirety or a part of DHPS may be collectively referred to as DHPSes in the cancer determination method of the present invention.

Firstly, the DHPSes level of a test sample is determined. When the determined DHPSes level is greater than a standard DHPSes level of a subject exhibiting no digestive system cancer (hereinafter, the subject may be also be referred to as a digestive system cancer-free subject in the cancer determination method of the present invention), an increase in expression of the DHPS gene of a test subject from which the test sample has been obtained (hereinafter may be also referred to as test sample donor) is confirmed. On the basis of the increase as an index, digestive system cancer of the test sample donor can be determined.

Examples of the test sample which may be used in the cancer determination method include blood specimens such as a serum specimen, a plasma specimen, and a whole blood specimen, and urine specimens. Of these, blood specimens are preferred. Also, such blood specimens may be subjected in advance to an appropriate treatment such as a treatment with heparin.

The standard DHPSes level of a digestive system cancer-free subject (including a cut-off value) may be determined by making a sample group of subjects which have not been found to exhibit digestive system cancer in a general inspection; determining the DHPSes levels of samples obtained from the sample group; and subjecting the determined DHPSes levels to statistical processing, to thereby obtain the average, standard deviation, etc. thereof.

No particular limitation is imposed on the method of determining the DHPSes level of a test sample. Examples of the determination method include a quantification method employing an antibody (preferably a monoclonal antibody) which specifically binds to DHPSes. Specific examples include immunoprecipitation, western blotting, immunostaining, EIA, RIA, turbidimetry, nephelometry, latex agglutination turbidimetry, and CLEIA. Alternatively, the DHPSes level may be directly determined through TOF-MASS. Among EIA techniques, ELISA employing an immobilized antibody is particularly preferred. Any of these quantification methods may be carried out through a technique which is established for quantifying DHPSes in a test sample as a quantification target substance. Some of these quantification methods will next be described briefly.

In one mode of the quantification means based on ELISA, a test sample is brought into contact with DHPS antibody immobilized on a microplate, to thereby bind DHPSes present in the test sample to the immobilized antibody. The DHPSes bound to the immobilized antibody is detected with another DHPS-antibody labelled with an enzyme or the like, whereby the quantification can be performed. Alternatively, the DHPSes level of the test sample may be determined through simultaneous reaction of the immobilized antibody, the test sample, and the enzyme-labelled antibody.

In one mode of the quantification means based on immunoprecipitation, a test sample is brought into contact with a DHPS antibody immobilized on beads, to thereby bind DHPSes in the test sample to the immobilized antibody, and the DHPSes bound to the immobilized antibody is separated. The DHPSes in the separated product is detected, whereby the quantification can be performed. The DHPSes quantification method based on immunoprecipitation may be carried out by subjecting the aforementioned separated product to electrophoresis, and causing a labelled DHPS antibody to react with a transferred electrophoresis pattern, to thereby detect bands attributed to DHPSes (i.e., western blotting).

The quantification may also be carried out through a method based on western blotting. In one specific mode, cells are removed from a test sample, and the cell-removed test sample is directly separated through electrophoresis. A labelled DHPS-antibody is caused to act on the transferred product thereof, and bands attributed to DHPSes are detected, to thereby quantify DHPSes in the test sample.

In one mode of the quantification means based on latex agglutination turbidimetry, a test sample is brought into contact with the DHPS-antibody bound to latex particles, to thereby form an aggregate of an immune complex through antigen-antibody reaction in the liquid phase, and the turbidity change is measured, whereby the quantification can be performed.

(3) Cancer Determination Method 2 of the Present Invention

The cancer determination method 2 of the present invention is a method, characterized in that expression of the DHPS gene is confirmed in a test sample, and digestive system cancer of a test subject from which the test sample has been obtained is determined on the basis of an increase in the gene expression as an index, wherein expression of the DHPS gene (a target gene) is confirmed by detecting a DHPS-antibody (an autoantibody) present in the test sample.

That is, the DHPS autoantibody level of a test sample is determined. When the determined DHPS autoantibody level is greater than a standard DHPS autoantibody level of a digestive system cancer-free subject, an increase in expression of the DHPS gene of a test subject from which the test sample has been obtained is confirmed. On the basis of the increase as an index, digestive system cancer of the test sample donor can be determined. Examples of the test sample which may be used in the cancer determination method include blood specimens such as a serum specimen, a plasma specimen, and a whole blood specimen, and urine specimens. Of these, blood specimens are preferred. Also, such blood specimens may be subjected in advance to an appropriate treatment such as a treatment with heparin.

The standard DHPS autoantibody level of a digestive system cancer-free subject (including a cut-off value) may be determined by making a sample group of subjects which have not been found to exhibit digestive system cancer in a general inspection; determining the DHPS autoantibody levels of test samples obtained from the sample group; and subjecting the determined DHPS autoantibody levels to statistical processing, to thereby obtain the average, standard deviation, etc. thereof.

The DHPS autoantibody level may be determined by, for example, bringing the test sample into contact with an immobilized polypeptide including DHPSes, and detecting, as a signal, a bond between the antibody (autoantibody) against DHPS present in the test sample and the immobilized polypeptide. Specific examples of the quantification method which may be employed in the invention include indirect immunofluorescence, ELISA, western blotting (immunoblotting), turbidimetry, nephelometry, latex agglutination turbidimetry, and CLEIA. Any of these quantification methods may be carried out through a technique which is established for quantifying DHPS autoantibody in a test sample as a quantification target substance. One mode of indirect immunofluorescence (FANA) includes bringing a test sample into contact with a DHPSes-immobilized protein array; binding the immobilized DHPSes to a DHPS antibody in the test sample, to thereby form an immobilized DHPSes-anti-DHPS antibody complex; and bringing the complex into contact with a fluorescent-labelled secondary antibody, to thereby quantify the DHPS autoantibody. In ELISA, quantification is carried out by using an enzyme label instead of the label of the secondary antibody employed in indirect immunofluorescence. A variety of labels may be chosen for the secondary antibody. One mode of western blotting include subjecting DHPSes to electrophoresis on SDS-polyacrylamide gel; transferring the electrophoresis results from the gel to a substrate (e.g., a nitrocellulose membrane); bringing a test sample into contact with the transfer substrate, to thereby form a complex between DHPSes on the transfer substrate and the DHPS antibody present in the test sample; and detecting the complex, whereby the quantification can be performed. In one mode of turbidimetry or nephelometry, a DHPSes-anti-DHPS antibody complex, formed via contact of a test sample with DHPSes, is detected by turbidity (turbidimetry) or a change in scattered light intensity (nephelometry), whereby the quantification can be performed. In one mode of latex agglutination turbidimetry, a test sample is brought into contact with DHPSes-bound latex particles, to thereby form an aggregate of latex particles via interaction between autoantibodies bound to latex particles, and the aggregate is detected, whereby the quantification can be performed. In one mode of CLEIA, a test sample is brought into contact with DHPSes-bound magnetic particles, to thereby form a DHPSes-anti-DHPS antibody complex on the magnetic particles, these particles are magnetically collected, unreacted matter is removed, and an appropriate fluorescent treatment or the like is carried out to detect the complex, whereby the quantification can be performed.

(4) Cancer Determination Method 3 of the Present Invention

A characteristic feature of the cancer determination method 3 of the present invention resides in that the method comprises detecting expression of a DHPS gene in a test sample, and determining digestive system cancer of a test subject from which the test sample has been obtained, on the basis of an increase in the gene expression as an index, wherein expression of the DHPS gene (i.e., a target gene) is confirmed by detecting, as a target nucleic acid, the entirety or a part of the DHPS gene, or a nucleic acid complementary to the entirety or a part of the DHPS gene, present in the test sample.

In one specific procedure, the level of mRNA encoding DHPSes in the test sample is determined. When the determined mRNA level is greater than a standard mRNA level of a digestive system cancer-free subject, an increase in expression of the DHPSes gene of a test subject from which the test sample has been obtained is confirmed. On the basis of the increase as an index, digestive system cancer of the test sample donor can be determined. Examples of the test sample which may be used in the cancer determination method include blood specimens such as a serum specimen, a plasma specimen, and a whole blood specimen, and urine specimens. Of these, blood specimens are preferred. Also, such blood specimens may be subjected in advance to an appropriate treatment such as a treatment with heparin.

The nucleic acid, serving as a basic material in the determination of the level of mRNA encoding DHPSes in the test sample, may be produced by extracting RNA from the test sample through a known technique and reversely transcribing the RNA to the corresponding DNA, to thereby yield a cDNA. The cDNA is subjected to gene amplification such as PCR employing a gene amplification primer for amplifying the DHPSes gene (RT-PCR). Through measuring the mRNA level equivalent (e.g., the copy number of the DHPSes gene in gene amplification at specific cycles, or an increasing rate of the DHPSes gene copy number) as a basic index, the expression level of the DHPSes gene in the test sample can be determined.

The target nucleic acid may be detected by hybridizing a nucleic acid probe including a nucleic acid fragment having a nucleotide sequence complementary to the nucleotide sequence of the target nucleic acid, with the target nucleic acid obtained as an immobilized or non-immobilized gene amplification product, and detecting the signal attributed to hybridization.

The signal may be detected through, for example, southern blotting. Alternatively, a series of steps of the cancer determination method 3 of the present invention may be carried out through, for example, a real-time analysis employing RT-PCR.

(5) Cancer Detection Kit of the Present Invention

As described above, the cancer detection kit of the present invention is a kit having elements for carrying out the cancer determination method of the present invention. The elements of the cancer detection kit vary in accordance with the mode and purpose of use of the cancer determination method of the present invention, the degree of kit design, and other factors.

In one mode of the cancer detection kit for carrying out the cancer determination method 1 of the present invention, the kit is employed for ELISA, which kit includes a plate on which a DHPS-antibody is immobilized as a primary antibody, a labelled secondary antibody, and an agent for developing the label of the secondary antibody.

Alternatively, the kit is employed for latex agglutination turbidimetry, which kit contains latex particles onto which a DHPS-antibody is bound. Yet alternatively, the kit is employed for CLEIA, which kit includes magnetic particles onto which a DHPS-antibody is bound, a labelled secondary antibody, and an agent for developing the label of the secondary antibody. The above-mentioned elements of the kits are merely examples, and the present invention also encompasses kits for carrying out other embodiments of the cancer determination method 1 of the present invention. Furthermore, it is possible for a similar kit having fewer elements so as to shear with an outsourcing inspection and to self-procurement. Also, another possible embodiment of the kit of the invention is a cancer detection kit which has further elements such as a diluent and a tube for an agent, so as to be immediately used. Needless to say, the kit may further include an additional element suited for a specific inspection procedure.

In one mode of the cancer detection kit for carrying out the cancer determination method 2 of the present invention, the kit is employed for FANA or ELISA, which kit includes a plate on which a DHPSes is immobilized, a labelled secondary antibody against the autoantibody, and an agent for developing the label of the secondary antibody. Alternatively, the kit is employed for latex agglutination turbidimetry, which kit contains latex particles onto which a DHPSes is bound. Yet alternatively, the kit is employed for CLEIA, which kit includes magnetic particles onto which a DHPSes is bound, a labelled secondary antibody against the autoantibody, and an agent for developing the label of the secondary antibody. The above-mentioned elements of the kits are merely examples, and the present invention also encompasses kits for carrying out other embodiments of the cancer determination method 2 of the present invention. Furthermore, it is possible for a similar kit having fewer elements so as to shear with an outsourcing inspection and to self-procurement. Also, another possible embodiment of the kit of the invention is a cancer detection kit which has further elements such as a diluent and a tube for an agent, so as to be immediately used. Needless to say, the kit may further include an additional element suited for a specific inspection procedure.

In one mode of the cancer detection kit for carrying out the cancer determination method 3 of the present invention, the kit may include a reverse transcriptase and a reverse transcription primer for reverse transcription of mRNA, a gene amplification primer for amplifying a cDNA encoding DHPSes, a nucleic acid probe for detecting the gene amplification product, and an agent for developing the signal of the nucleic acid probe. The above-mentioned elements of the kits are merely examples, and the present invention also encompasses kits for carrying out other embodiments of the cancer determination method 3 of the present invention.

Furthermore, it is possible for a similar kit having fewer elements so as to shear with an outsourcing inspection and to self-procurement. Also, another possible embodiment of the kit of the invention is a cancer detection kit which has further elements such as a diluent and a tube for an agent, so as to be immediately used. Needless to say, the kit may further include an additional element suited for a specific inspection procedure.

EXAMPLES

The present invention will next be described by way of examples.

[A] Arteriosclerosis Determination Method of the Present Invention

[Reference Example] Screening of DHPS as Arteriosclerosis Marker (1) Blood serum specimens of arteriosclerosis patients and a healthy subject were brought into contact with a protein array on which about 8,000 proteins were immobilized. Autoantibodies which are intrinsic to arteriosclerosis patients and which are present in the specimens were detected through indirect immunofluorescence. As a result, about 150 autoantibody candidates were specified. A certain species of the candidates is an autoantibody against DHPS in a serum specimen. The serum specimens of the arteriosclerosis patients were obtained from carotid artery stenosis patients diagnosed by a hospital and other facilities relating to the research.

The above assessment of the patients employed a control group including normal test subjects (n: almost the same as the number of arteriosclerosis patients) having the same sex and age (±5) selected from outpatients of the above facilities. Upon consultation of the target outpatients and hospitalization of the patients, all the patients were subjected to the following procedure: 1) providing the patient or a member of his or her family with guidance in relation to the purpose and voluntariness of the research, and the like, to obtain informed consent; 2) inquiring medical history (the patients and the family), habits (drinking, smoking, etc.), and working style; 3) collecting blood, separating the blood sample to serum and hematocytes, and individually storing them under freezing; and 4) recording the clinical severity, therapy history, findings in a blood test, etc. on the basis of the doctor's medical records. After serum separation, the blood samples of the analysis targets were stored at −80° C. before start of the experiments. Substantially the same procedure regarding a test subject as described above was employed in the Examples mentioned below.

(2) Next, the aforementioned about 150 autoantibody candidates were subjected to screening through ELISA. Before carrying out ELISA of each autoantibody candidate, about 150 antigen proteins including DHPS were produced as recombinant proteins through the following steps.

Firstly, an insert was produced through PCR. In a specific procedure, a primer having a restriction enzyme recognition site suited for gene recombination to an expression vector pET28 or pGEX-4T was produced in advance. Reverse transcription PCR was carried out by use of RNA extracted from osteosarcoma cell line U2-OS as a template, to thereby yield cDNA, and PCR was repeated, to thereby produce a full-length insert. The thus-produced insert and an expression vector were treated with restriction enzymes, and the insert was ligated with the expression vector by means of Ligation-Convenience Kit (product of Nippon Gene Co., Ltd.), to thereby produce a plasmid including the insert. *E. coli* competent cells BL21 (product of Nippon Gene Co., Ltd.) was transformed by use of the plasmid. The thus-obtained transformant was cultured in an LB medium containing an antibiotic. By use of IPTG, production of an insert DNA-originating protein via gene expression was induced. The thus-transformed *E. coli* cells were centrifuged, and the recovered product was further separated into soluble fractions and insoluble fractions. The insoluble fractions were solubilized with urea. The thus-obtained protein was purified with ProBond Resin (product of Invitrogen) and Glutathione-Sepharose (product of GE Healthcare).

Through the above procedure, a plurality of purified recombinant proteins were produced, and then injected to a 96-well ELISA plate at 5 μg/mL. The well was maintained overnight at 4° C. so as to immobilize the proteins on the plate. Thus, a 96-well ELISA plate for use in ELISA on which recombinant proteins were immobilized was produced.

In the ELISA procedure, the recombinant protein-immobilized plate was washed with PBS and blocked with a solution containing 20% sugar and 20% synthetic polymer (product of NOF Corporation). Then, the immobilized proteins were reacted with a 200-fold dilution of a serum sample of a patient or a control serum (a serum sample of a healthy subject). Subsequently, the plate was washed with PBS, and an HRP-labelled goat anti-human IgG antibody was added to the plate. Finally, an enzyme chromogenic substrate was added to the plate, and the absorbance (OD) of the developed color was measured by means of a plate reader at a wavelength of 450 nm.

As a result of the screening based on ELISA, about 40 members of the about 150 autoantibody (antigen protein) candidates were selected. The about 40 candidates included DHPS (i.e., subject matter of the present invention). Actually, autoantibodies against proteins other than DHPS were also studied. However, only the case of DHPS is disclosed herein.

[Example A-1] Studies on Autoantibody Through ELISA

Studies through ELISA were performed three times.
(a) Studies on Autoantibody Through ELISA (1)

Serum specimens of acute cerebral infarction patients (78 cases) and those of healthy subjects (51 cases) obtained from a medical facility A were employed. FIGS. 1 and 2 show the results. FIG. 1 is a graph showing DHPS autoantibody titers of serum specimen of acute cerebral infarction patients (patient group) and healthy subjects (normal group), with distribution profiles thereof. FIG. 2 is a graph showing ROC (receiver operation characteristic) curves regarding the distribution profiles.

Table 1 shows the statistical test results obtained from FIGS. 1 and 2. As shown in Table 1, the cut-off value was found to be about 0.69, represented by a dotted line in FIG. 1.

TABLE 1

| Normal | No. of specimens | 51 |
|---|---|---|
|  | Average | 0.57 |
|  | SD | 0.63 |
|  | Cut-off | 0.69 |
| Patients | No. of specimens | 78 |
|  | Average. | 2.62 |
|  | SD | 3.87 |

TABLE 1-continued

| Results | P value | <0.001 |
|---|---|---|
|  | % Positive | 69% |

The P value was smaller than 0.05 (0.01), indicating that "the serum antibody titer against DHPS is significantly greater in the arteriosclerosis patient group than that in the healthy subject group."

The percent positive at the above cut-off value was about 69%.
(b) Studies on Autoantibody Through ELISA (2)

Serum specimens of acute cerebral infarction patients (111 cases) obtained from a medical facility B, and those of acute cerebral infarction patients (46 cases) obtained from a medical facility C (the total no. of cases: 157), and those of healthy subjects (51 cases) obtained from the medical facility A were employed. FIGS. 3 and 4 show the results. FIG. 3 is a graph showing DHPS autoantibody titers of serum specimen of acute cerebral infarction patients (patient group) and healthy subjects (normal group), with distribution profiles thereof. FIG. 4 is a graph showing ROC (receiver operation characteristic) curves regarding the distribution profiles.

Table 2 shows the statistical test results obtained from FIGS. 3 and 4. As shown in Table 2, the cut-off value was found to be about 0.69, represented by a dotted line in FIG. 3.

TABLE 2

| Normal | No. of specimens | 51 |
|---|---|---|
|  | Average | 0.57 |
|  | SD | 0.63 |
|  | Cut-off | 0.69 |
| Patients | No. of specimens | 157 |
|  | Average | 2.73 |
|  | SD | 5.35 |
| Results | P value | <0.001 |
|  | % Positive | 73% |

The P value was considerably smaller than 0.05 (0.01), indicating that "the serum antibody titer against DHPS is significantly greater in the arteriosclerosis patient group than that in the healthy subject group."

The percent positive at the above cut-off value was about 73%.
(c) Studies on Autoantibody Through ELISA (3)

In studies (c), the behavior of a DHPS autoantibody marker was investigated in known arteriosclerosis marker-positive and -negative groups, respectively. CRP was used as the known arteriosclerosis marker. CRP (C-reactive protein) is an acute-phase protein (acute phase reactant: APR) and was found by Tillet and other researchers in 1930, as a serum protein which causes sedimentation reaction with a C polysaccharide extracted from *Diplococcus pneumoniae* (*Streptococcus pneumoniae*). Some studies in recent years have revealed that, when an inflammation associated with arteriosclerosis occurs in the vascular tissue, CRP is produced in the liver by the action of an inflammatory cytokine secreted from inflammatory cells which infiltrate an arteriosclerosis site, thereby elevating the CRP level. The studies have also revealed that the CRP concentration correlates with the severity of the functional disorder of the vascular endothelium, and that an increase in CRP level is a risk factor for causing angina and myocardial infarction (Ridker P. M., Circulation 103: 1813, 2002).

The specimens for CRP measurement which were employed in studies (c) were serum specimens of acute cerebral infarction patients (65 cases) and those of healthy subjects (18 cases) obtained from a medical facility A (the total number of the specimens: 83). Each of the specimens was subjected to a CRP assay through latex agglutination turbidimetry by means of a C-reactive protein kit (Nanopia, product of Sekisui Medical Co., Ltd.). The results were categorized on the basis of a CRP cut-off value of 0.2 mg/dL. More specifically, when the CRP level of a specimen was higher than 0.2 mg/dL, the specimen was categorized into a "CRP arteriosclerosis risk group," whereas when the CRP level of a specimen was 0.2 mg/dL or lower, the specimen was categorized into a "CRP arteriosclerosis non-risk group." Each CRP risk group was divided into the patient group and the healthy group, and the DHPS autoantibody titer of a serum specimen was determined through ELISA in each group. FIG. 5 shows the results. Also, FIG. 6 shows an ROC curve of the CRP arteriosclerosis non-risk group having a CRP level of 0.2 mg/dL or lower.

The P value was 0.003, which is definitely smaller than 0.05 (0.01).

The percent positive was 46%. Thus, even in the case of a group assessed to have a low risk of arteriosclerosis through CRP level, arteriosclerosis can be significantly detected through an arteriosclerosis test by use of DHPS.

No significance test was conducted for a "CRP arteriosclerosis risk group," since the number of the specimens of the normal group was insufficient. However, as is clear from FIG. 5, determination of a DHPS autoantibody is also effective for detecting arteriosclerosis in the risk group.

[Example A-2] Studies on Autoantibody Through Western Blotting

An insert was produced through the procedure shown in Reference Example (2) above, and purified proteins were produced in the same manner. In a specific procedure, a primer having a restriction enzyme recognition site suited for gene recombination to an expression vector pET28 or pGEX-4T was produced in advance. Reverse transcription PCR was carried out by use of RNA extracted from osteosarcoma cell line U2-OS as a template, to thereby yield cDNA, and PCR was repeated, to thereby produce a full-length insert. The thus-produced insert and an expression vector were treated with restriction enzymes, and the insert was ligated with the expression vector by means of Ligation-Convenience Kit (product of Nippon Gene Co., Ltd.), to thereby produce a plasmid including the insert. $E.\ coli$ competent cells BL21 (product of Nippon Gene Co., Ltd.) was transformed by use of the plasmid. The thus-obtained transformant was cultured in an LB medium containing an antibiotic. By use of IPTG, production of an insert DNA-originating protein via gene expression was induced. The thus-transformed $E.\ coli$ cells were centrifuged, and the recovered product was further separated into soluble fractions and insoluble fractions. The insoluble fractions were solubilized with urea. The thus-obtained protein was purified with ProBond Resin (product of Invitrogen) and Glutathione-Sepharose (product of GE Healthcare).

Each purified protein produced through the above procedure was denatured with an SDS sample buffer, to thereby prepare a western blotting sample. The sample was subjected to electrophoresis on 12% polyacrylamide gel, and the obtained protein pattern was transferred to a nitrocellulose membrane by means of a pattern-transfer apparatus. The transferred protein was blocked with 5% skim milk, and 500-fold diluted serum samples of patients (specimens 1 to 4) were added as primary antibodies to the membrane, followed by overnight incubation. Thereafter, the membrane was washed with PBST, and a 20,000-fold diluted HRP-labeled goat anti-human IgG antibody (ab98633, product of Abcam) was added to the membrane. After reaction for 30 minutes, the membrane was washed with PBST, and a luminescent reagent (Immobilon Western, product of MILLIPORE) was added thereto. A photographic film was exposed to the resultant luminescence and then developed.

FIG. 7 shows the results in an electrophoresis chart. As shown in FIG. 7, specimens 1, 2, 3, and 4 were serum specimens of acute cerebral infarction patients obtained from the medical facility A. ELISA measurements (autoantibody) in terms of protein His-DHPS (a.a. 184-369) were 3.61 (specimen 1), 3.82 (specimen 2), 3.61 (specimen 3), and 3.47 (specimen 4). ELISA measurements (autoantibody) in terms of protein GST-DHPS (a.a. 183-369) were 3.60 (specimen 1), 2.64 (specimen 2), 2.33 (specimen 3), and 2.46 (specimen 4).

The following Tables 3-1 to 3-4 show detected band intensities as relative values with respect to the band intensity of each membrane marker (75 kDa) as "1." Table 3-1 shows the results of specimen 1, Table 3-2 shows the results of specimen 2, Table 3-3 shows the results of specimen 3, and Table 3-4 shows the results of specimen 4. In the Tables, protein His-DHPS (a.a. 184-369) is abbreviated as His-36C, and protein GST-DHPS (a.a. 183-369) is abbreviated as GST-36C.

TABLE 3-1

| U1 | 75 kDa Marker | 1.00 |
| U2 | GST-36C | 3.19 |
| U3 | His-36C | 8.08 |

TABLE 3-2

| U1 | 75 kDa Marker | 1.00 |
| U2 | GST-36C | 1.20 |
| U3 | His-36C | 4.52 |

TABLE 3-3

| U1 | 75 kDa Marker | 1.00 |
| U2 | GST-36C | 0.49 |
| U3 | His-36C | 5.29 |

TABLE 3-4

| U1 | 75 kDa Marker | 1.00 |
| U2 | GST-36C | 0.12 |
| U3 | His-36C | 2.46 |

The above results have revealed that the autoantibodies present in the specimens 1, 2, 3, and 4—serum specimens of acute cerebral infarction patients—were found to exhibit strong reactivity to protein His-DHPS (a.a. 184-369). As a result of the western blotting analysis, reaction between the target bands with the autoantibodies was confirmed. In addition, the obtained band intensities have revealed that specimens having a greater measurement in ELISA exhibited higher reactivity to protein His-DHPS (a.a. 184-369).

Next, the presence of endogenous DHPS in each specimen was investigated through western blotting by use of an anti-DHPS-antibody. In a specific procedure, each of the His-DHPS (SEQ ID NO: 1, a.a. 1-369) protein (positive control) and the serum specimens of patients (specimens 1 to 4) was denatured with an SDS sample buffer, to thereby prepare a western blotting sample. The sample was subjected to electrophoresis on 10% polyacrylamide gel, and the obtained protein pattern was transferred to a nitrocellulose membrane by means of a pattern-transfer apparatus. The transferred protein was blocked with 5% skim milk, and a 500-fold diluted anti-DHPS-antibody (H00001725-B02P, product of Abnova) was added as a primary antibody to the membrane, followed by overnight incubation. Thereafter, the membrane was washed with PBST, and a 7,500-fold diluted HRP-labeled sheep anti-mouse IgG antibody (NA931, product of GE Healthcare) was added to the membrane. After reaction for 30 minutes, the membrane was washed with PBST, and a luminescent reagent (Immobilon Western, product of MILLIPORE) was added thereto. A photographic film was exposed to the resultant luminescence and then developed.

The results are shown in an electrophoresis diagram of FIG. 8. As is clear from FIG. 8, the presence of a band suggesting the presence of endogenous DHPS was confirmed in all specimens. Thus, the results strongly suggested the presence of endogenous DHPS in blood.

[B] Cancer Determination Method of the Present Invention

[Example B-1] Studies on Autoantibody Through ELISA (1) Method of Investigation

Antigen proteins against a DHPS-autoantibody were produced as recombinant proteins through the following steps.

Firstly, an insert was produced through PCR. In a specific procedure, a primer having a restriction enzyme recognition site suited for gene recombination to an expression vector pET28 or pGEX-4T was produced in advance. Reverse transcription PCR was carried out by use of RNA extracted from osteosarcoma cell line U2-OS as a template, to thereby yield cDNA, and PCR was repeated, to thereby produce a full-length insert. The thus-produced insert and an expression vector were treated with restriction enzymes, and the insert was ligated with the expression vector by means of Ligation-Convenience Kit (product of Nippon Gene Co., Ltd.), to thereby produce a plasmid including the insert. *E. coli* competent cells BL21 (product of Nippon Gene Co., Ltd.) was transformed by use of the plasmid. The thus-obtained transformant was cultured in an LB medium containing an antibiotic. By use of IPTG, production of an insert DNA-originating protein via gene expression was induced. The thus-transformed *E. coli* cells were centrifuged, and the recovered product was further separated into soluble fractions and insoluble fractions. The insoluble fractions were solubilized with urea. The thus-obtained protein was purified with ProBond Resin (product of Invitrogen) and Glutathione-Sepharose (product of GE Healthcare).

Through the above procedure, a plurality of purified recombinant proteins were produced, and then injected to a 96-well ELISA plate at 10 μg/mL. The well was maintained overnight at 4° C. so as to immobilize the proteins on the plate. Thus, a 96-well ELISA plate for use in ELISA on which recombinant proteins were immobilized was produced.

In the ELISA procedure, the recombinant protein-immobilized plate was washed with PBS and blocked with 10% fetal bovine serum PBS. Then, the immobilized proteins were reacted with a 2,000-fold dilution of a serum sample of a patient or a control serum (a serum sample of a healthy subject). Subsequently, the plate was washed with PBS, and an HRP-labelled goat anti-human IgG antibody was added to the plate. Finally, an enzyme chromogenic substrate was added to the plate, and the absorbance (OD) of the developed color was measured by means of a plate reader at a wavelength of 450 nm.

(2) Studies on Autoantibody Through ELISA

Serum specimens of esophageal cancer patients (61 cases) and colorectal cancer patients (19 cases) (total n: 80) obtained from a medical facility D, and those of healthy subjects (51 cases) obtained from a medical facility A were employed. FIGS. 9 and 10 show the results. FIG. 9 is a graph showing DHPS autoantibody titers of cancer patients (patient group) and healthy subjects (normal group), with distribution profiles thereof. FIG. 10 is a graph showing ROC (receiver operation characteristic) curves regarding the distribution profiles.

Table 4 shows the statistical test results obtained from FIGS. 9 and 10. As shown in Table 4, the cut-off value was found to be about 0.69, represented by a dotted line in FIG. 9.

TABLE 4

| Normal | No. of specimens | 51 |
|---|---|---|
| | Average | 0.57 |
| | SD | 0.63 |
| | Cut-off | 0.69 |
| Patients | No. of specimens | 80 |
| | Average | 3.82 |
| | SD | 8.18 |
| Results | P value | <0.001 |
| | % Positive | 80% |

The P value was smaller than 0.05, indicating that "the serum antibody titer against DHPS is significantly greater in the esophageal cancer and colorectal cancer patient group than that in the healthy subject group."

The percent positive at the above cut-off value was about 80%.

The invention claimed is:

1. A method for detecting anti-deoxyhypusine synthase autoantibody in a subject, wherein said method comprises:
   detecting, in a blood, serum, or plasma sample from a test subject, the amount of anti-deoxyhypusine synthase autoantibody, wherein said autoantibody is able to bind to a polypeptide consisting of the amino acid sequence of SEQ ID NO: 1.

2. The method according to claim 1, wherein said detecting comprises contacting said test sample with an immobilized polypeptide comprising the amino acid sequence of SEQ ID NO: 1, or comprising the amino acid sequence of residues 184-369 of SEQ ID NO: 1; and when said test sample contains antibody that binds to said immobilized polypeptide, binding between the antibody and the immobilized polypeptide is detected as a signal.

3. The method according to claim 1, wherein the amount of the anti-deoxyhypusine synthase autoantibody is determined by performing enzyme-linked immunosorbent assay (ELISA), enzyme immunoassay (EIA), radioimmunoassay (RIA), western blotting, turbidimetry, nephelometry, latex agglutination turbidimetry, or chemiluminescence enzyme immunoassay (CLEIA).

4. The method according to claim 3, wherein the amount of the anti-deoxyhypusine synthase autoantibody is determined by performing enzyme immunoassay (EIA).

5. The method according to claim 3, wherein the amount of the anti-deoxyhypusine synthase autoantibody is determined by performing enzyme-linked immunosorbent assay (ELISA).

* * * * *

SEQUENCE LISTING

<160> NUMBER OF SEQ ID NOS: 2

<210> SEQ ID NO 1
<211> LENGTH: 369
<212> TYPE: PRT
<213> ORGANISM: Homo sapiens

<400> SEQUENCE: 1

Met Glu Gly Ser Leu Glu Arg Glu Ala Pro Ala Gly Ala Leu Ala Ala
1               5                   10                  15

```
Val Leu Lys His Ser Ser Thr Leu Pro Pro Glu Ser Thr Gln Val Arg
             20                  25                  30

Gly Tyr Asp Phe Asn Arg Gly Val Asn Tyr Arg Ala Leu Leu Glu Ala
         35                  40                  45

Phe Gly Thr Thr Gly Phe Gln Ala Thr Asn Phe Gly Arg Ala Val Gln
 50                  55                  60

Gln Val Asn Ala Met Ile Glu Lys Lys Leu Glu Pro Leu Ser Gln Asp
 65                  70                  75                  80

Glu Asp Gln His Ala Asp Leu Thr Gln Ser Arg Arg Pro Leu Thr Ser
             85                  90                  95

Cys Thr Ile Phe Leu Gly Tyr Thr Ser Asn Leu Ile Ser Ser Gly Ile
            100                 105                 110

Arg Glu Thr Ile Arg Tyr Leu Val Gln His Asn Met Val Asp Val Leu
            115                 120                 125

Val Thr Thr Ala Gly Gly Val Glu Glu Asp Leu Ile Lys Cys Leu Ala
        130                 135                 140

Pro Thr Tyr Leu Gly Glu Phe Ser Leu Arg Gly Lys Glu Leu Arg Glu
145                 150                 155                 160

Asn Gly Ile Asn Arg Ile Gly Asn Leu Leu Val Pro Asn Glu Asn Tyr
                165                 170                 175

Cys Lys Phe Glu Asp Trp Leu Met Pro Ile Leu Asp Gln Met Val Met
            180                 185                 190

Glu Gln Asn Thr Glu Gly Val Lys Trp Thr Pro Ser Lys Met Ile Ala
            195                 200                 205

Arg Leu Gly Lys Glu Ile Asn Asn Pro Glu Ser Val Tyr Tyr Trp Ala
        210                 215                 220

Gln Lys Asn His Ile Pro Val Phe Ser Pro Ala Leu Thr Asp Gly Ser
225                 230                 235                 240

Leu Gly Asp Met Ile Phe Phe His Ser Tyr Lys Asn Pro Gly Leu Val
                245                 250                 255

Leu Asp Ile Val Glu Asp Leu Arg Leu Ile Asn Thr Gln Ala Ile Phe
            260                 265                 270

Ala Lys Cys Thr Gly Met Ile Ile Leu Gly Gly Gly Val Val Lys His
            275                 280                 285

His Ile Ala Asn Ala Asn Leu Met Arg Asn Gly Ala Asp Tyr Ala Val
        290                 295                 300

Tyr Ile Asn Thr Ala Gln Glu Phe Asp Gly Ser Asp Ser Gly Ala Arg
305                 310                 315                 320

Pro Asp Glu Ala Val Ser Trp Gly Lys Ile Arg Val Asp Ala Gln Pro
                325                 330                 335

Val Lys Val Tyr Ala Asp Ala Ser Leu Val Phe Pro Leu Leu Val Ala
            340                 345                 350

Glu Thr Phe Ala Gln Lys Met Asp Ala Phe Met His Glu Lys Asn Glu
        355                 360                 365

Asp

<210> SEQ ID NO 2
<211> LENGTH: 1110
<212> TYPE: DNA
<213> ORGANISM: Homo sapiens

<400> SEQUENCE: 2
atggaaggtt ccctggaacg ggaggcgcca gcgggggcgc tggccgccgt gctaaagcac      60
```

-continued

```
agctcgacgt tgccgcccga aagcacccag gtccggggct acgacttcaa ccgcggtgtg    120
aattaccgcg cactgctgga ggccttcggc accaccggct tccaagcaac caacttcggg    180
cgcgctgtac agcaagtcaa tgccatgatc gagaagaagc tggaaccact gtcacaggat    240
gaagaccagc acgcggacct gacccagagc cgccgcccac ttaccagctg caccattttc    300
ctgggatata catccaacct catcagttca ggcatccgtg agaccattcg ctaccttgtg    360
cagcacaaca tggtggacgt attggtgacc acagctggcg gcgtggagga agacctcatc    420
aagtgcctgg cgcccacata cttgggcgag tttagcctca gggggaagga gctccgggag    480
aacgggatca ataggatcgg aaacctgctg gtgcccaatg agaattactg caagtttgag    540
gactggctga tgcccattct ggaccagatg gtgatggagc agaacacaga gggtgtaaag    600
tggacgcctt ctaagatgat cgcccggctg ggcaaggaga tcaacaaccc agagtccgtg    660
tattactggg cccagaagaa ccacatccct gtgtttagtc ccgcacttac agacggctcg    720
ctgggcgaca tgatcttctt ccattcctac aagaacccgg gcctggtcct ggacatcgtt    780
gaggacctga ggctcatcaa cacacaggcc atctttgcca agtgcactgg gatgatcatt    840
ctgggcgggg gcgtggtcaa gcaccacatt gccaatgcca acctcatgcg gaacggggcc    900
gactacgctg tttacatcaa cacagcccag gagtttgatg gctctgactc aggtgcccga    960
ccagacgagg ctgtctcctg gggcaagatc cgggtggatg cacagcccgt caaggtctat   1020
gctgacgcct ccctggtctt cccctgctt gtggctgaaa cctttgccca gaagatggat   1080
gccttcatgc atgagaagaa cgaggactga                                    1110
```